United States Patent
Lou et al.

(10) Patent No.: US 9,198,588 B2
(45) Date of Patent: Dec. 1, 2015

(54) FREQUENCY-ADAPTIVE NOTCH FILTER

(71) Applicant: Welch Allyn, Inc., Skaneateles Falls, NY (US)

(72) Inventors: Yaolong Lou, Singapore (SG); Yong Sern Gwee, Singapore (SG); Peter Glocker, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 275 days.

(21) Appl. No.: 13/665,226

(22) Filed: Oct. 31, 2012

(65) Prior Publication Data

US 2014/0121548 A1    May 1, 2014

(51) Int. Cl.
*G06F 17/10* (2006.01)
*A61B 5/0402* (2006.01)
*H03H 21/00* (2006.01)
*A61B 5/00* (2006.01)

(52) U.S. Cl.
CPC .............. *A61B 5/0402* (2013.01); *A61B 5/7203* (2013.01); *A61B 5/725* (2013.01); *H03H 21/0021* (2013.01)

(58) Field of Classification Search
CPC .......... H03H 21/0012; H03H 17/0294; H03H 21/0043; H04B 3/23; H04L 25/03043
USPC .......................................... 708/322; 375/350
See application file for complete search history.

(56) References Cited

U.S. PATENT DOCUMENTS

| | | |
|---|---|---|
| 2007/0110263 A1 | 5/2007 | Brox |
| 2008/0275353 A1 | 11/2008 | Bartal et al. |
| 2010/0014685 A1* | 1/2010 | Wurm ..................... 381/71.11 |
| 2011/0066052 A1 | 3/2011 | Mascarenhas |
| 2011/0144460 A1 | 6/2011 | Oh et al. |
| 2011/0319777 A1 | 12/2011 | Mehrotra et al. |

OTHER PUBLICATIONS

International Search Report and Written Opinion in PCT/US2013/066554 mailed Feb. 25, 2014, 14 pages.

* cited by examiner

*Primary Examiner* — Tan V. Mai
(74) *Attorney, Agent, or Firm* — Merchant & Gould P.C.

(57) ABSTRACT

One apparatus includes a notch filter that has a state observer unit and a parameter adaptation unit. The state observer unit is configured to receive a sampled noisy electrical signal and a sampled filtered electrical signal, the state observer unit having an estimated noise signal output, the estimated noise signal output carrying an estimated noise signal to be subtracted from the sampled noisy electrical signal, resulting in the filtered electrical signal. The parameter adaptation unit is configured to receive the estimated noise signal and an error signal from the state observer unit. The parameter adaptation unit is also configured to determine, based on the estimated noise signal and the error signal, an updated estimated noise frequency, thereby causing the state observer unit to generate an updated estimated noise signal to be provided on the estimated noise signal output.

9 Claims, 31 Drawing Sheets

FREQUENCY-ADAPTIVE NOTCH FILTER

BACKGROUND

Sinusoidal noise exists in many systems. For instance, the input signals for medical devices, such as an electrocardiograph (ECG), are often interfered with by electrical power supply line networks. For another instance, the read/write head in a disk drive deviates from the desired tracking trajectory due to disk eccentricity. This interference, or deviation, is generally caused by sinusoidal noise.

In each of these types of systems, it is desirable to eliminate such spurious signals, and isolate the desired signal, so that the output of a circuit which processes the signal is a true representation of the input signal without noise. In general, there are two methods to remove sinusoidal noise in a system. One method is to insert a notch filter at the noise frequency in series into the signal flow path. Another method is to detect the sinusoidal noise, and then to subtract it from the contaminated signal.

Both the serial notch filter and the signal subtraction methods of removing sinusoidal noise have drawbacks. For example, one problem with using a serial notch filter is that with the elimination of noise at the notch frequency, the frequency component of the desired signal at the notch frequency is eliminated as well. This is particularly unacceptable in ECG, where any clinical information of the patient, including signals at the filtered frequency, should be examined as the base for diagnostic and treatment. In addition, using serial notch filters in ECG applications can cause ringing in the ECG waveform, which can result in an incorrect interpretation and/or analysis of the ECG signal.

In the noise subtraction method, there are generally three approaches in implementation: Adaptive Noise Cancelling (ANC), Adaptive Feedforward Cancellation (AFC) and Internal Mode. Adaptive Noise Cancelling, in which the noise is considered uncorrelated with the input signal but correlated with a known reference signal, generally averages the signal over some amount of time to cancel the noise. This ANC approach relies upon an additional reference signal that may or may not be known, and also relies on an averaging approach in the concept of least-square. However, averaging signal over time is considered to risk change of some signal characteristic, e. g. removal or distortion of nonrepetitive signals, which may bear clinically relevant physiological dynamic information of the original ECG signal.

In Adaptive Feedforward Cancellation, noise is canceled by a signal expressed as a linear combination of sine and cosine regressors and two unknown parameters, in which the amplitude and phase of the sinusoidal noise are embedded. With this linear feature, an adaptive rule is designed to update the unknown parameters, thereby causing the output of the signal to converge to the noise in amplitude and phase. The regressors that have the noise frequency information embedded are usually implemented by look-up tables. Using this AFC approach, however, different look-up tables are needed for noises with different frequencies. For example, to estimate the higher harmonic noises, two additional look-up tables are needed for every harmonic, thereby rendering such implementations complex and expensive.

The Internal Mode approach uses trigonometric features to generate a sinusoidal signal that holds the information of amplitude and phase in the mode itself. The frequency information expressed in a parameter in the internal mode is generally required to be known and preset. Because the frequency is preset, it is claimed that this internal model is equivalent to a standard notch filter and does not provide for parameter adaptation.

From the functional point of view, all above described approaches can be seen as notch filters in the sense that they attempt to remove the noise signal at the notch frequency.

Apart from the various problems with the methods described above, a common precondition to employing any of the above-described methods is that the frequency of the noise signal to be detected and removed is both constant and known. However, this requirement of prior knowledge for the noise frequency cannot always be met. In some cases, the noise frequency may change, and may be unknown to the user. For example, in the case of power line interference observed on ECG signals, for instance, there are different power line frequencies in different regions. For example, 60 Hz is used in North America, whereas 50 Hz in Europe and China. Because ECG users cannot be assumed to know the power line frequencies present in a particular region, and because the same ECG machine might be used or sold in different regions, ECG manufacturers are generally required to create systems that are capable of being used in any region.

One particular example of the output of an ECG machine is illustrated in FIG. 1. That figure illustrates an ECG report 10 for an ECG signal taken using a portable ECG CP50 machine manufactured by Welch Allyn, Inc. of Skaneateles Falls, N.Y. That device uses the internal mode approach, similar to that discussed above, in which a sinusoidal noise at a preset frequency (60 Hz in this example) signal can be filtered. In this example, the ECG is used in a country having a 50 Hz power supply. As illustrated, the ECG report shows power line noises (illustrated best in the magnified portion 12 of the report 10) that are not eliminated because of the difference between the preset frequency to the internal mode and the local power line frequency. As discussed above, the internal mode, as well as the various other approaches for removing periodic noise, are not well adapted to this scenario, in which differing power signal frequencies may be encountered.

In addition to the problem of power signals having different intended frequencies, it is also possible for some variance in a power line frequency to occur. For example, Standard EN50160 specifies a maximum power network frequency variations in countries forming the European Union (EU) as ±1% for 95% of a week, and +4%, −6% for a full week. This means that networks in EU might have a frequency variation of about 4% high, or 6% low, for periods of up to 5% of a week, that is, 8.5 hours. Moreover, there are some parts of the world where the electrical power supply is even worse, resulting in larger frequency variations than those specified in existing regional standards.

For these and other reasons, improvements in existing ECG machines and noise filters are desired.

SUMMARY

In accordance with the following disclosure, the above and other issues are generally addressed by the following.

In a first aspect, a notch filter has a state observer unit and a parameter adaptation unit. The state observer unit is configured to receive a sampled noisy electrical signal and a sampled filtered electrical signal, the state observer unit having an estimated noise signal output, the estimated noise signal output carrying an estimated noise signal to be subtracted from the sampled noisy electrical signal, resulting in the filtered electrical signal. The parameter adaptation unit is configured to receive the estimated noise signal and an error signal from the state observer unit. The parameter adaptation unit is also configured to determine, based on the estimated noise signal and the error signal, an updated estimated noise frequency, thereby causing the state observer unit to generate an updated estimated noise signal to be provided on the estimated noise signal output.

In a second aspect, a method of stably adaptively detecting sinusoidal noise from an electrical signal is disclosed. The method includes receiving a noisy electrical signal having a periodic noise component with an unknown and time-varying frequency and a filtered electrical signal component. The method also includes performing a frequency identification process on the sampled noisy electrical signal to determine a baseline frequency on which frequency variations occur for an estimated periodic noise signal, the frequency identification process selecting from among a plurality of discrete, predetermined frequencies. The method further includes performing a frequency adaptation process on the sampled noisy electrical signal, the frequency adaptation process resulting in an updated estimated periodic noise signal to be subtracted from the sampled noisy electrical signal, thereby forming a filtered electrical signal.

In a third aspect, an ECG machine is disclosed. The ECG machine includes a controller, one or more ECG sensor inputs communicatively connected to the controller, and a power signal electrically connected to the controller. The ECG machine also includes a memory configured to store computer-executable instructions which, when executed using the controller, are configured to perform a method. The method includes receiving a noisy electrical signal at the controller from the one or more ECG sensor inputs, the noisy electrical signal having a periodic noise component occurring at least in part due to the power line network interference and a filtered electrical signal component. The method further includes performing a frequency identification process on the sampled noisy electrical signal to determine a baseline frequency on which frequency variations occur for an estimated periodic noise signal, the frequency identification process selecting from among a plurality of discrete, predetermined frequencies. The method also includes performing a frequency adaptation process on the sampled noisy electrical signal, the frequency adaptation process resulting in an updated estimated periodic noise signal to be subtracted from the sampled noisy electrical signal, thereby forming a filtered electrical signal.

DETAILED DESCRIPTION

As briefly described above, embodiments of the present disclosure are directed to digital signal processing or filtering, and more particularly, to filters for removing noise components of a signal (e.g., a sinusoidal signal). Still more particularly, embodiments discussed herein provide for a method and apparatus for removing sinusoidal noise with unknown and time-varying frequency, such as via use of a frequency-adaptive notch filter.

In accordance with the apparatus and methods described herein it is noted that, using the adaptive notch-filtering described herein it is possible to eliminate sinusoidal noise, in particular, to remove the interference in ECG measurement due to power line network interference. This can be performed by automatically identifying the frequency of the power line network that interferes with the ECG measurement, thereby allowing for use of a common device within devices under power line networks with different frequencies, and despite variation in frequency of the power line network, without interference that would otherwise arise due to its occurrence outside of a notch filter's frequency band.

In addition to the flexibility for use with different constant-frequency power signals, the adaptive apparatus disclosed herein is configured to adaptively track variation of the power line frequency to remove the interference. In certain embodiments, an apparatus constructed according to the principles discussed herein can adapt to differing power line frequencies without requiring user knowledge of the power line frequency or input into the device, and is constructed to automatically remove the power line interference as the filter is being turned on.

Figure 2:
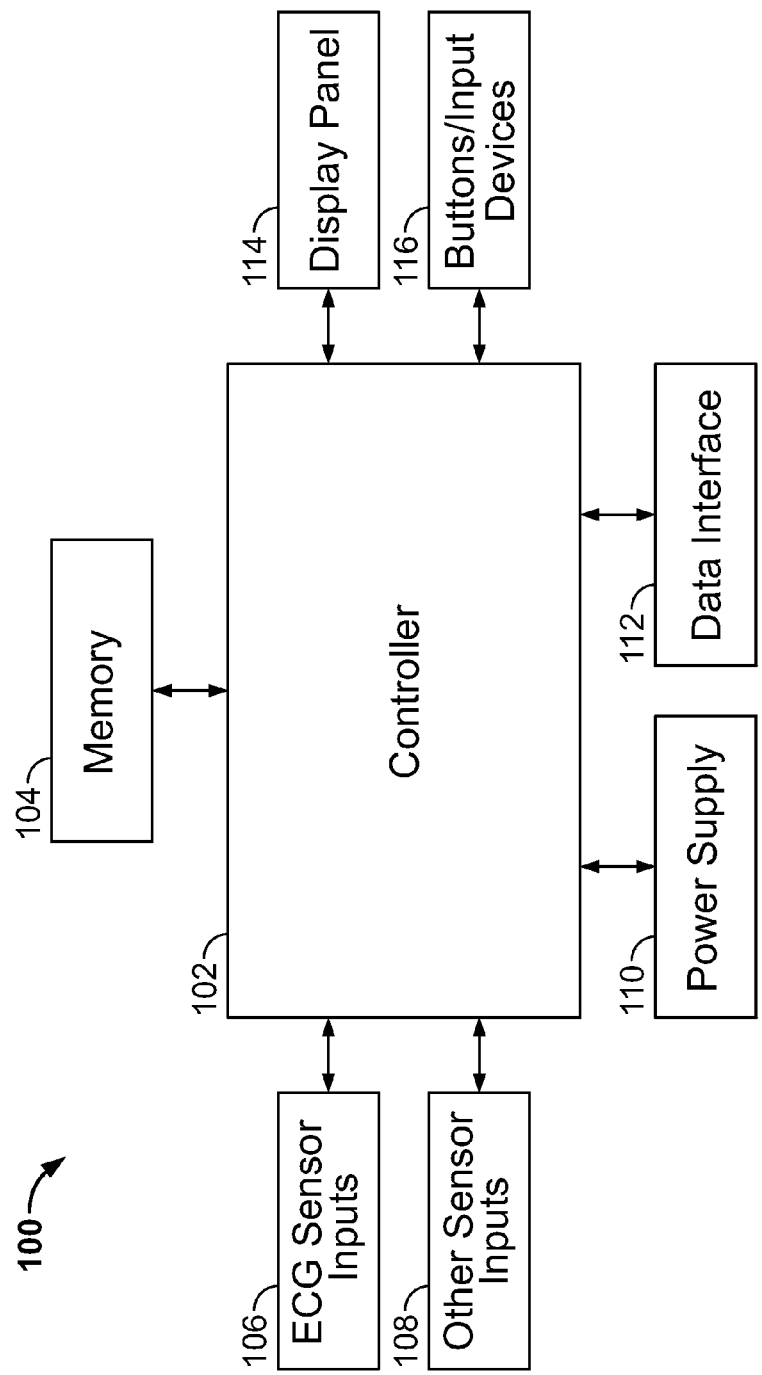
FIG. 2 shows an example block diagram of an ECG machine in which aspects of the present disclosure can be implemented.

Referring now to FIG. 2, an example block diagram of an ECG machine 100 is shown, in which aspects of the present disclosure can be implemented. The ECG machine 100 is generally configured to obtain a signature representing electrical activity of a heart over a period of time. Generally, an ECG machine is configured to detect very low level electrical signals in a human body over time, based on the use of electrodes attached to a user's skin. The ECG machine can generally take any of a number of forms; example ECG machines could be a CP50, CP100/200 or CP150/250 machine manufactured by Welch Allyn, Inc. of Skaneateles Falls, N.Y., as adapted to incorporate the adaptive sinusoidal interference cancellation features described herein.

In the embodiment shown, the ECG machine 100 includes a controller 102 communicatively connected to a memory 104. The controller 102 is generally configured as a physical device including one or more integrated circuit configured to execute software instructions. In various embodiments, the controller 102 can include one or more general purpose processing units, or can alternatively be implemented as an application-specific integrated circuit (ASIC). The memory 104 can take any of a number of forms, and can include volatile and/or non-volatile memory units, forming computer-readable media from which the controller 102 can access data and/or instructions for execution.

In the embodiment shown, the ECG machine 100 further includes inputs, including ECG sensor inputs 106 and other sensor inputs 108. The ECG sensor inputs 106 can be connected, for example, to electrodes configured to be placed on a human, such that the electrodes can detect and communicate electrical signals to the controller 102 for processing. In example embodiments, the ECG sensor inputs 106 and other sensor inputs 108 can be connected to general purpose or specialized I/O connections of the controller 102.

In the embodiment shown, the ECG machine 100 includes a power supply 110, configured to provide power to the controller 102 and other components of the ECG machine 100. In various embodiments, the power supply 110 can be configured for connection to an external power signal, such as a 50 Hz or 60 Hz signal, and can also be configured to charge or provide power from a battery unit (integrated therewith) for powering the ECG machine 100 if it is to be used in circumstances where a power signal is unavailable.

Figure 1:
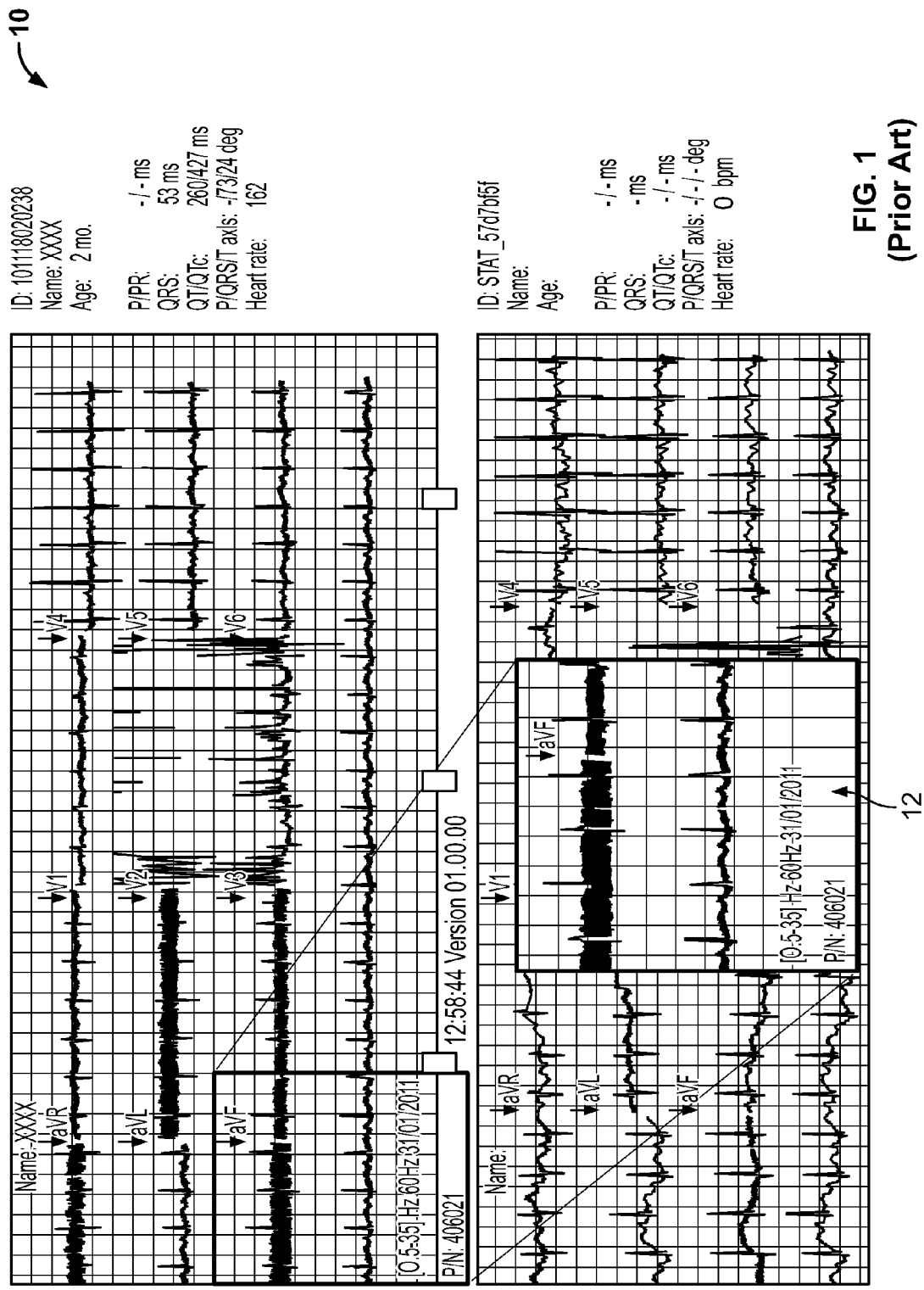
FIG. 1 shows an example ECG chart in which power line interference at a frequency of 50 Hz in an ECG signal is not eliminated by a notch filter set at an incorrect frequency of 60 Hz.

In the embodiment shown, the ECG machine 100 also includes a data interface 112, which can be any of a variety of I/O interfaces, such as a Universal Serial Bus (USB) or serial data connection, and can be configured for exchange of data between the ECG machine 100 and an external system. In addition, as illustrated the ECG machine 100 includes a display panel 114 and one or more input devices 116 for user interaction with the machine, for example to provide commands to the machine directing particular display or test functionality. In some embodiments, the display panel 114 can be any of a variety of types of LCD, LED, plasma, printer, plotter or other types of displays, and is configured to display one or more ECG graphs, such as that illustrated in FIG. 1.

In accordance with the present disclosure, it is noted that, due to the sensitive electrical signals received at the ECG sensor inputs 106 at the controller 102, it is not uncommon to have some type of electrical crosstalk or interference, due in part to power line noise incurred based on the interaction of an ECG machine, patient body, and the interconnection between the two. For example, an ECG measurement from an ECG machine powered by battery experiences interference due to a power line signal received at the ECG machine. In such cases, and as noted above, it is common to filter or otherwise compensate for that ECG signal, when the signal is with a noise of a known magnitude/frequency. In accordance with the following disclosure, the ECG machine 100 can include, either within the controller 102 or the memory 104, instructions or circuitry configured to compensate for such interference, for example by adaptively detecting a frequency of the interfering signal, and applying a compensation or filtering arrangement at that frequency.

In accordance with the ECG machine 100 described above, and also as discussed throughout the present disclosure, the term computer readable media as used herein may include computer storage media and communication media.

As used in this document, a computer storage medium is a device or article of manufacture that stores data and/or computer-executable instructions. Computer storage media may include volatile and nonvolatile, removable and non-removable devices or articles of manufacture implemented in any method or technology for storage of information, such as computer readable instructions, data structures, program modules, or other data. By way of example, and not limitation, computer storage media may include dynamic random access memory (DRAM), double data rate synchronous dynamic random access memory (DDR SDRAM), reduced latency DRAM, DDR2 SDRAM, DDR3 SDRAM, DDR4 SDRAM, solid state memory, read-only memory (ROM), electrically-erasable programmable ROM, optical discs (e.g., CD-ROMs, DVDs, etc.), magnetic disks (e.g., hard disks, floppy disks, etc.), magnetic tapes, and other types of devices and/or articles of manufacture that store data. Computer storage media generally excludes transitory wired or wireless signals.

Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

Figure 3:
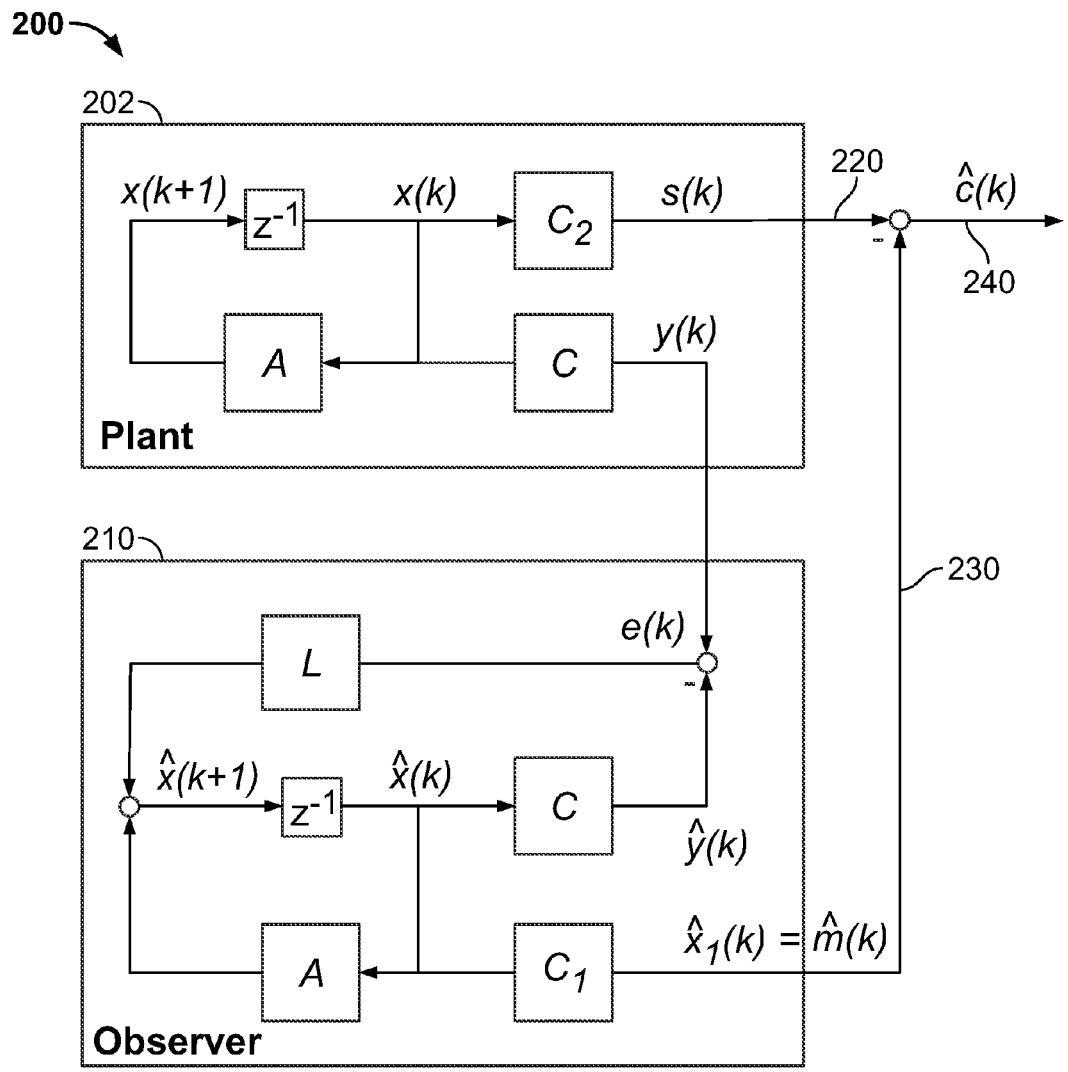
FIG. 3 shows an example block diagram of a system including a state observer useable to remove sinusoidal noise of a known frequency from a signal, which can be used to implement example aspects of the present disclosure.

Referring now to FIG. 3, a system 200 comprising a state space model of the noisy interference as plant 202, in which the noise is modeled as one of the system state, and a state observer 210 to estimate the noise useable to remove sinusoidal noise of a known frequency from a signal is disclosed, and upon which the adaptive state observer (and associated adaptive notch filter) of the present disclosure are based. Generally, the state observer 210 can be implemented as part of an adaptive observer or adaptive filter arrangement in software and/or hardware of an ECG machine, such as machine 100 described above, and can be used to detect a particular sinusoidal interference signal.

Overall, the system 200 is configured to deal with a signal and view that signal as an aggregate of an ECG signal and a sinusoidal noise signal. In general, a sinusoidal signal m(t), which may have an amplitude A, angle frequency ω, and phase φ can be expressed as:

$$m(t)=A\sin(\omega t+\phi).$$

In a discrete domain, this signal can alternatively be represented by the following equation, where m(k) is the k-th sample of m(t), $N=2\cos(2\pi f/f_s)$, $\omega=2\pi f$, and $f_s$ is the sampling frequency:

$$m(k)=Nm(k-1)-m(k-2)$$

It is noted that in this equation, the amplitude and phase do not explicitly appear; but are instead embedded in this characteristic called internal mode. The only one parameter that needs to be set is ω or N, which is determined by the frequency. This feature is therefore used to generate a sinusoidal signal.

In FIG. 3, the system 200 includes a plant 202 and an observer 210. The plant 202 represents a system from which a noisy electrical signal can be obtained; in general, the plant 202 generates the ECG signal as affected by a power line interference signal or other periodic signal, resulting in noisy signal 220. In the context of FIG. 3, this noisy signal is represented by s(k), with the ECG signal and power line interference components are represented as c(k) and m(k), respectively:

$$s(k)=c(k)+m(k)$$

It is noted that, over time, each sampled power line interference signal can have a modeled as a function of the previous power line interference as follows, where w represents the relationship between the power line frequency $f_n$ and sampling frequency, $f_s$, $w=2\cos(2\pi f_n/f_s)$:

$$m(k+1)=wm(k)-m(k-1).$$

Similarly, if the ECG signal c(k) has a very slowly changing dynamics based on the means described later such that it can be modeled as a constant offset of c(k)=c(k−1), the output can be represented by the following equation:

$$y(k)=s(k)-s(k-1)=m(k)-m(k-1)+c(k)-c(k-1).$$

The plant 202 describing by the above equations can be reformulated as a state space model:

$$x(k+1)=Ax(k),$$

$$y(k)=Cx(k),$$

in which the system state is illustrated as x(k) and the following model assumptions are present:

$$x(k) = \begin{bmatrix} m(k) \\ m(k-1) \\ c(k) \\ c(k-1) \end{bmatrix},$$

$$A = \begin{bmatrix} w & -1 & 0 & 0 \\ 1 & 0 & 0 & 0 \\ 0 & 0 & 1 & 0 \\ 0 & 0 & 0 & 1 \end{bmatrix},$$

$$C = [1 \; -1 \; 1 \; -1]$$

The observer 210 is configured to receive a version of this noisy signal 220, in the form of the y(k) signal. The observer 210 can be constructed in a variety of ways; in one example embodiment, the observer 210 can be represented as an observed system state $\hat{x}(k)$, an observed output $\hat{y}(k)$, and a measured error e(k):

$$\hat{x}(k+1)=A\hat{x}(k)+Le(k),$$

$$\hat{y}(k)=C\hat{x}(k),$$

$$e(k)=y(k)-\hat{y}(k)$$

In this arrangement, $\hat{x}(k)=[\hat{m}(k)\;\hat{m}(k-1)\;\hat{c}(k)\;\hat{c}(k-1)]^T$ and L is the observer gain, $L=[1\;0\;0\;0]^T$. This observer 210 can alternatively be reflected as:

$$\hat{m}(k+1)=w\hat{m}(k)-\hat{m}(k-1)+le(k)$$

Once the system state $\hat{x}(k)$ is estimated by the observer, an estimated noise 230 can be obtained from the following:

$$\hat{m}(k)=C_1\hat{x}(k), \; C_2=[1\;0\;0\;0]$$

This estimated noise 230 is generally subtracted from the noised signal 220, thereby resulting in a de-noised ECG signal 240:

$$\hat{c}(k)=s(k)-\hat{m}(k)=C_2x(k)-C_1\hat{x}(k), \; C_2=[1\;0\;1\;0].$$

Figure 4:
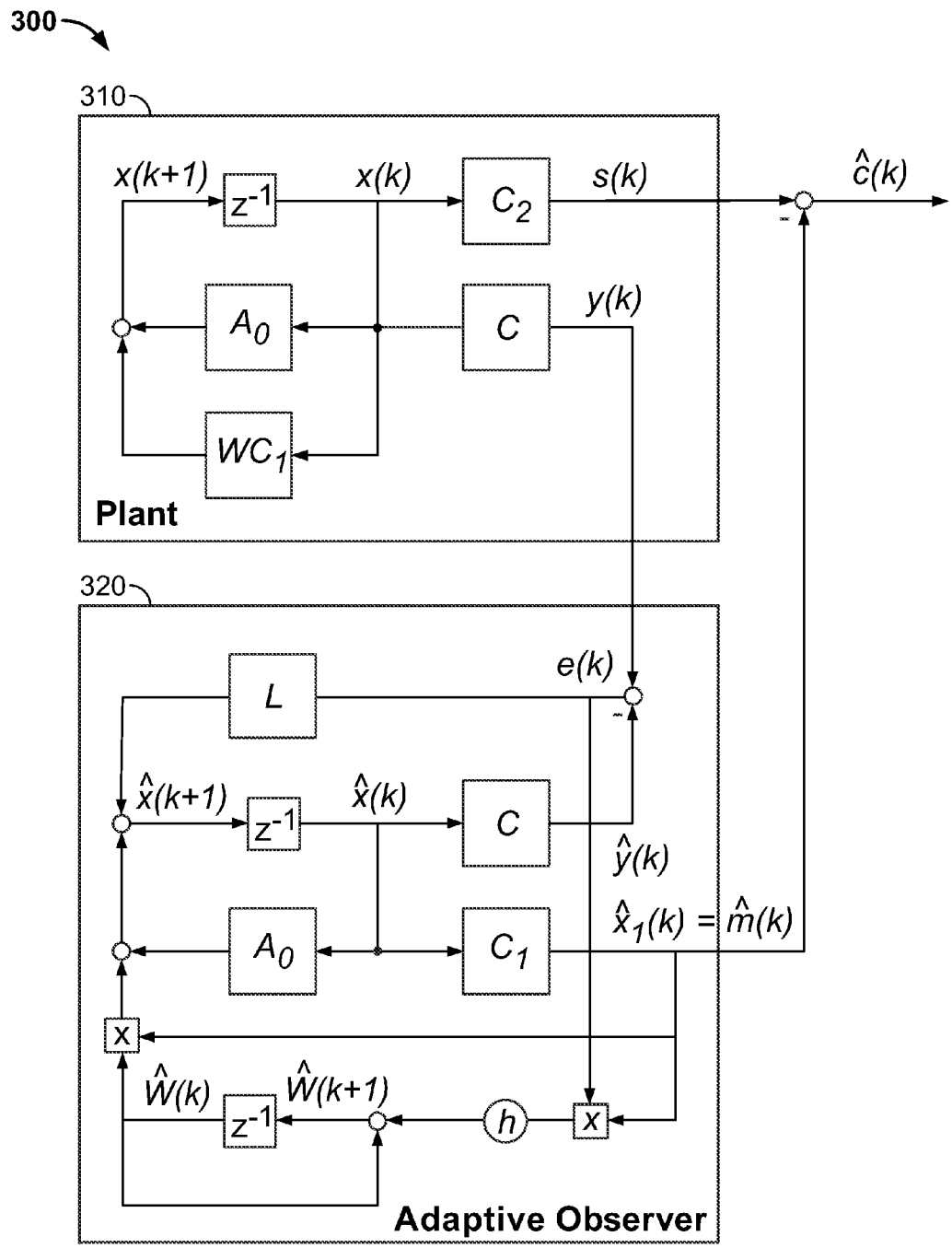
FIG. 4 shows an example block diagram of a system including a frequency adaptive state observer removing sinusoidal noise with an unknown and time-varying frequency, according to an example embodiment.

Now referring to FIG. 4, an adaptive system 300 is illustrated, which can be used to isolate and remove sinusoidal noise with an unknown and time-varying frequency, according to an example embodiment. In this arrangement, a plant 310 is illustrated whose model further includes W, an unknown parameter vector representing the unknown and time-varying frequency, and the system state including the noise is observed by a frequency adaptive state observer 320. As compared to the arrangement of FIG. 3, when a sinusoidal signal is unknown, the state observer 320 can be used to estimate the noise signal that is taken as a system state by considering the de-noised ECG signal 240 (unaffected by a power line network interference) as modeled as a constant. In particular, as illustrated in FIG. 4, the unknown parameter is estimated as being linear in the error mode, and therefore a linear adaptive observer can be implemented, to ensure that both system state error and parameter estimation error generally converge to zero (i.e., over time, the estimation of the phase, frequency, and magnitude of the power signal contribution converges to an accurate value).

In the embodiment shown, the plant 310 is modeled in state space as $$x(k+1)=A_0x(k)+WC_1x(k)=A_0x(k)+Wx_1(k),$$

$$y(k)=Cx(k),$$

where $A=A_0+WC_1$, $A_0$ is known, W is unknown, $x_1(k)=C_1x(k)$, and $$A_0 = \begin{bmatrix} w_0 & -1 & 0 & 0 \\ 1 & 0 & 0 & 0 \\ 0 & 0 & 1 & 0 \\ 0 & 0 & 0 & 1 \end{bmatrix},$$

$$W = \begin{bmatrix} W \\ 0 \\ 0 \\ 0 \end{bmatrix},$$

$$C_1 = [1\;0\;0\;0].$$

The adaptive observer 320 can be constructed as follows:

$$\hat{x}(k+1)=A_0\hat{x}(k)+Le(k)+\hat{W}(k)\hat{x}_1(k),$$

$$\hat{y}(k)=C\hat{x}(k),$$

$$e(k)=y(k)-\hat{y}(k),$$

$$\hat{W}(k+1)=\hat{W}(k)+he(k)\hat{x}_1(k).$$

In the above, h>0 is a factor to control the parameter update speed and $\hat{W}(k)$ is the estimation of the unknown parameter W at the k-th sample, in other words: $\hat{W}(k)=[\hat{w}(k)\,0\,0\,0]^T$, and $\hat{x}_1(k)=C_1\hat{x}(k)$.

When the adaptive observer model 320 is expanded, the noise component of a particular sample can be represented as follows:

$$\hat{m}(k+1)=w_0\hat{m}(k)-\hat{m}(k-1)+le(k)+\hat{w}(k)\hat{m}(k).$$

Similarly, the frequency of the noise as observed at a particular sample can be tracked to vary over time, using the parameter update speed set above, as follows:

$$\hat{w}(k+1)=\hat{w}(k)+he(k)\hat{m}(k).$$

As compared to the state space observer 210 of FIG. 3, it is noted that observer 210 can be converted to an adaptive observer 320 by adding the last term $\hat{w}(k)\hat{m}(k)$ in the equation representing the sampled noise $\hat{m}(k+1)$ and adding the term $he(k)\hat{m}(k)$ to reflect the change in frequency based on the previous sampled noise, $\hat{w}(k+1)$. In general, and in view of the above, it can be proven that the adaptive observer 320 is stable in the sense that both the system error and the parameter adaptation error converge to zero over time.

Figure 5:
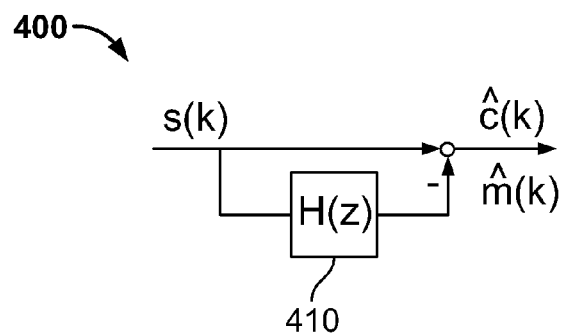
FIG. 5 shows an example block diagram of the equivalent adaptive notch filter of the adaptive state observer, according to an example embodiment.

Referring now to FIG. 5, a block diagram of an adaptive notch filter 400 is shown, implementing the adaptive state observer of FIG. 4 according to an example embodiment. In other words, a transfer function N(z) can be expressed as:

$$N(z)=\frac{\hat{c}(z)}{s(z)}=\frac{1}{1-H(z)}$$

In this equation, transfer function H(z), illustrated as transfer function 410 of FIG. 5, can be expressed as:

$$H(z)=\frac{\hat{m}(z)}{s(z)}=\frac{lz^{-1}-lz^{-2}}{1-(w_0+\hat{w}-l)z^{-1}+(1-l)z^{-2}}$$

resulting in:

$$N(s)=\frac{1}{1-H(z)}=\frac{1-(w_0+\hat{w}-l)z^{-1}+(1-l)z^{-2}}{1-(w_0+\hat{w})z^{-1}+z^{-2}}$$

This is, correspondingly, a notch filter whose notch frequency is represented by parameter $w_0+\hat{w}$. When the system is configured to be adaptable to update 4 over time, the filter becomes an adaptive notch filter, analogous to the construction illustrated in FIG. 4. Although it is functionally equivalent to a notch filter in the sense that the frequency component at the notch frequency is —suppressed in magnitude, it is different from the serial notch filter approach in which both the noise and the ECG signal at the notch frequency are decreased. Here only the noise signal is eliminated whereas the ECG signal is not affected.

Figure 6:
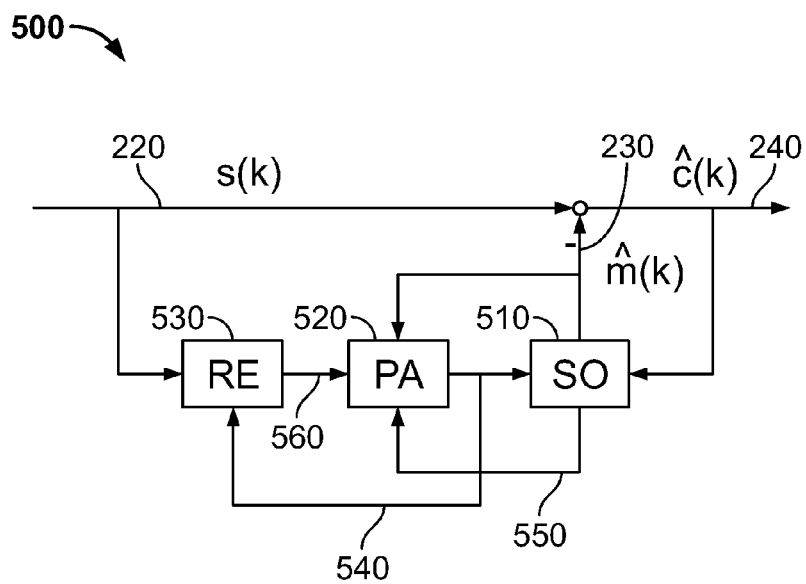
FIG. 6 shows an example block diagram of an upper-level structure of a frequency-adaptive notch filter, according to an example embodiment.

FIG. 6 is a block diagram of a top-level structure of a frequency-adaptive notch filter 500, according to an example embodiment. Generally, the filter 500 includes a state observer unit 510, a parameter adaptation unit 520, and a robustness enhancer unit 530. Generally, a de-noised ECG signal 240 is detected, similarly to the manner described above in connection with FIGS. 3-5, by subtracting an estimated noise 230 from a noisy ECG signal 220. In the embodiment shown, the state observer unit 510 receives the de-noised ECG signal 240, as well as an estimated noise frequency 540, output from the parameter adaptation unit 520. The state observer unit 510 generates an estimated noise signal 230 and an error 550, to be provided to the parameter adaptation unit 520. Additionally, the parameter adaptation unit 520 also receives an input 560 from the robustness enhancer unit 530. The robustness enhancer unit 530 receives the noisy signal 220, as well as the estimated frequency 540.

Figure 7:
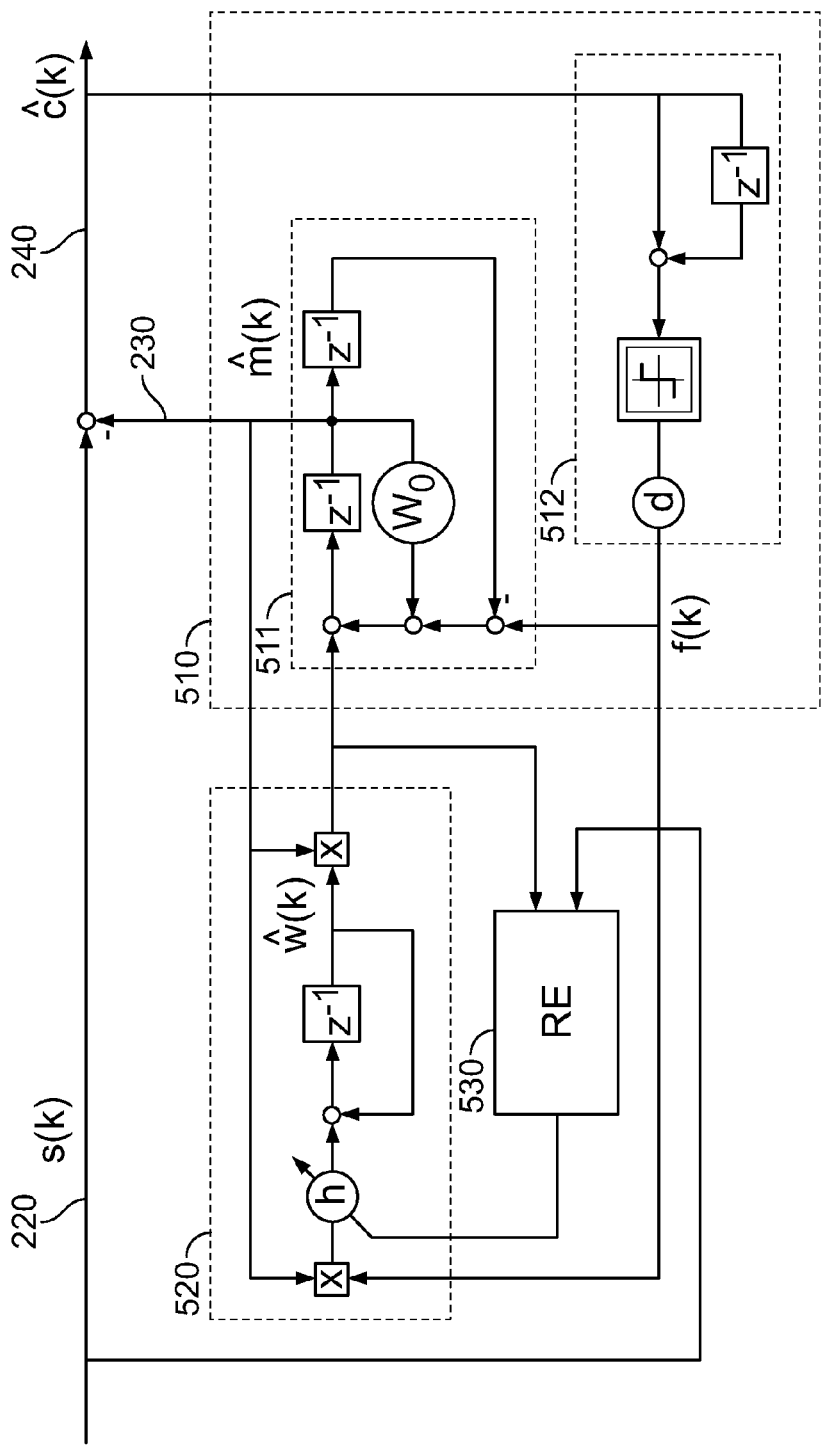
FIG. 7 depicts detailed structures of the state observer unit and the parameter adaptation unit of FIG. 6, according to an example embodiment.

FIG. 7 depicts detailed structures of the state observer unit 510 and the parameter adaptation unit 520, according to an example embodiment. In this example, the state observer unit 510 includes a sinusoidal internal model 511 and an error generator 512. In example embodiments, the sinusoidal model 511 can be described as $\hat{m}(k+1)=w_0\hat{m}(k)-\hat{m}(k-1)+\hat{w}(k)\hat{m}(k)+f(k)$, while the error generator 512 described by $f(k)=d\,\text{sgn}(\hat{c}(k)-\hat{c}(k-1))=d\,\text{sgn}(y(k)-\hat{y}(k))$ can be considered as the clamped output of the linear error with a very large observer gain l, i.e., $f(k)=le(k)=l(y(k)-\hat{y}(k))$, $|e(k)|\leq d/l$, where d is the error clamp. Furthermore, the parameter adaptation unit 520 can be described according to the adaptive observer equation explained above, namely $\hat{w}(k+1)=\hat{w}(k)+hf(k)\hat{m}(k)$.

Figure 8:
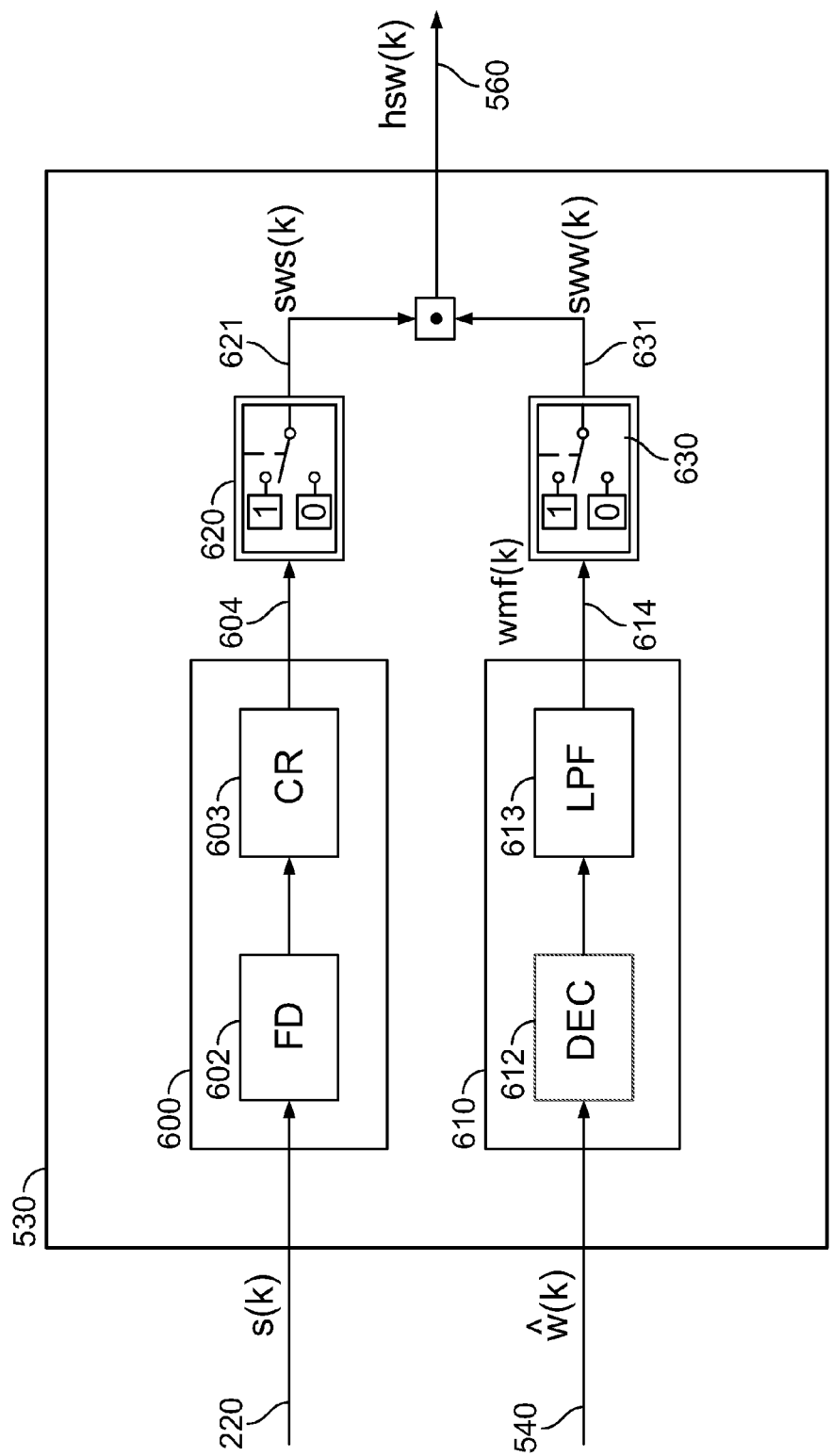
FIG. 8 depicts a detailed structure of the robustness enhancer unit of FIG. 6, according to an example embodiment.

FIG. 8 depicts a detailed structure of the robustness enhancer unit 530 of FIG. 6, according to an example embodiment. In the embodiment shown, the robustness enhancer unit 530 is generally constructed to enhance the robustness of the system adaptation, for example by controlling the manner by which system convergence to the unknown frequency takes place.

In an example embodiment of the robustness enhancer unit 530, a switch function method can be employed, in which a segment of the overall signal is sought that has relatively slow dynamics for system adaptation, and segments of the overall signal that have high dynamics are ignored. In other words, the robustness enhancer unit 530 controls a switching output that controls when the parameter adaptation unit 520 is active, thereby ensuring that parameter update occurs during quiet periods of the low dynamic portion of the signal, and allows, in the case of an ECG signal, parameter update to take place away from the ECG signal spikes that are naturally occurring based on cardiac activity. This is the basis of modeling the ECG signal as a constant offset during parameter update.

Although in general a variety of different approaches can be taken for detecting a slow dynamics portion of a signal using the robustness enhancer unit, in one example embodiment a max/min switching approach is used, that implements both a linear criterion unit 600 and a wide angle unit 610. In the embodiment shown, a linear criterion unit 600 can be used to look for a segment that has relatively low dynamics for system adaptation, and stop the adaptation at an observed segment that has high dynamics, while the wide angle unit is configured to overlook the parameter adaptation on a wider perspective. Details of each unit are provided below.

In an example embodiment, linear criterion unit 600 can be configured to use the noisy signal 220 as input and provide an output 604 that represents a local magnitude within an expected noise signal time difference. A switching unit 620 receives the output 604, and generates a switching output 621 with a logic value of "0" (indicating to stop adaptation) or "1" (indicating to continue adaptation). Generally, the linear criterion unit 600 includes one or more signal analysis functions which obtain an absolute value of signal magnitudes over a period of time greater than the ratio of the sampling frequency over the minimum noise frequency. In one such embodiment, these functions can be described as:

$$FD(k) = s(k+d_n) - s(k), \text{ for } k=1 \ldots d_n, d_n \geq f_s/f_{min}$$

$$CR = |FD_{max} - FD_{min}|$$

In this embodiment, the switching unit can selectively activate based on whether the magnitude of CR exceeds a predetermined threshold M which determines whether to stop parameter adaptation:

$$sws(k) = \begin{cases} 1, & \text{if } CR < M \\ 0, & \text{else} \end{cases}$$

In an example embodiment, the wide angle unit 610 includes a decimation element 612 and a low-pass filter 613. The decimation element 612 resamples the input parameter estimation 440 in a lower sampling frequency with decimation factor dm, and passes that resampled signal to the low-pass filter 613, which in turn removes high frequency signals.

In the embodiment shown, a second switching unit 630 receives an output signal from the wide angle unit 610, and, in one case, for example, in the frequency identification, outputs a binary value based on the filtered signal according to the following function:

$$sww(k) = \begin{cases} 0, & \text{if } wmf(k) \geq wmf_1 \text{ or } wmf(k) \leq wmf_2 \\ 1, & \text{else} \end{cases}$$

In considering the output of the second switching unit as a function of a rate of change of wmf, this rate of change can be expressed as:

$$dwmf(k) = wmf(k+1) - wmf(k),$$

Therefore, in another case, for example, in the frequency adaptation, the switch output of the second switching unit 630 can be expressed as a function of whether a rate of change exceeds a particular threshold:

$$sww(k) = \begin{cases} 0, & \text{if } |dwmf(k)| \leq \delta \\ 1, & \text{else} \end{cases}$$

Based on the above, an overall output from the robustness enhancer unit 530 is therefore a logical "AND" combination of switching units 620, 630, as follows:

$$hsw(k) = sws(k) \cdot sww(k).$$

This modulates the parameter adaptation by the following rate: $h = h \cdot hsw(k)$.

Figure 9:
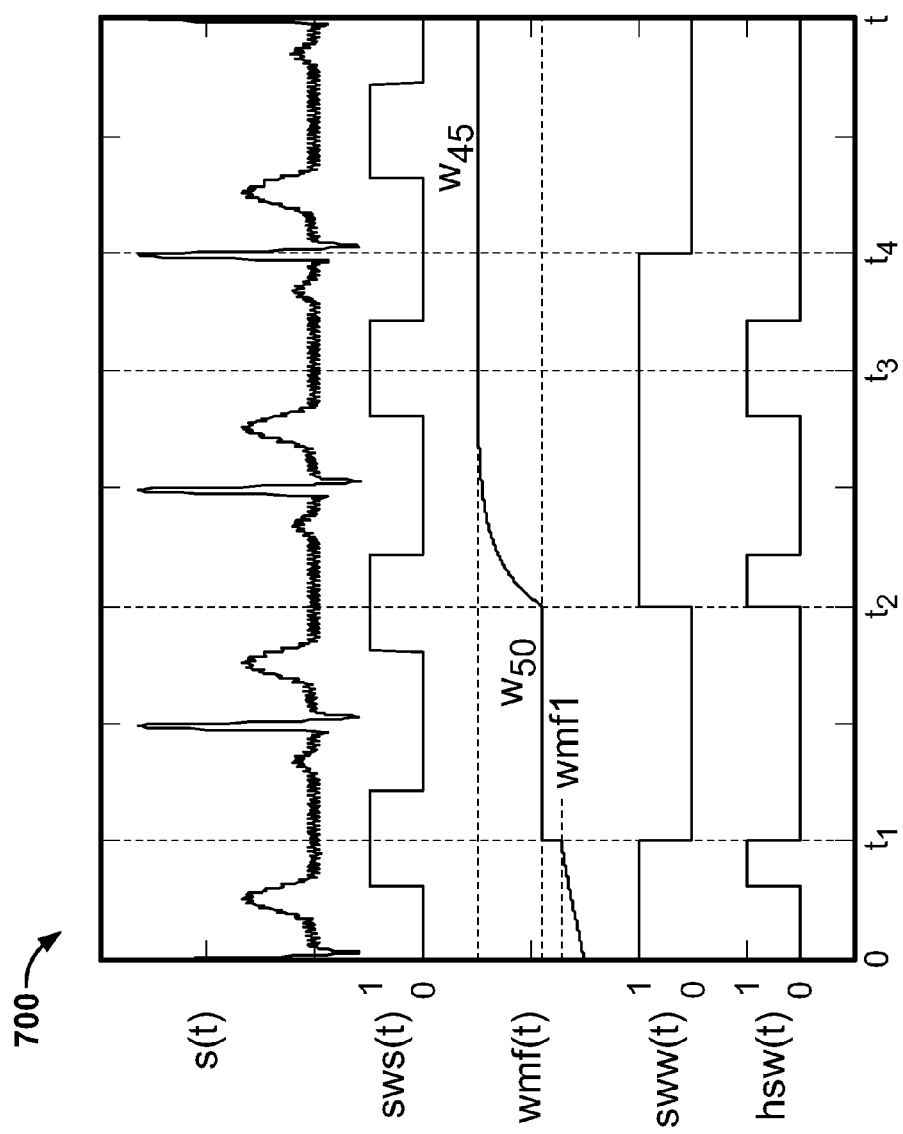
FIG. 9 shows a plurality of switch functions incorporated into the robustness enhancer unit, according to an example embodiment.

FIG. 9 shows a chart 700 that depicts a plurality of switch functions incorporated into the robustness enhancer unit, according to an example embodiment. In particular, the chart 700 illustrates switch functions that may occur to remove power line interference having a 50 Hz frequency, with up to 10% variations below that frequency value. As seen in that figure, output of the first switching unit 620, sws(k), configured to represent a high logic signal at a time where the noisy signal s (k) is relatively constant; in addition, the output of the second switching unit 630, sww(k), is configured to represent a high logic signal at a time where the rate of change of wmf is above a particular threshold. As such, where both of these features are occurring, the output of the robustness enhancer unit 530 enables adaptation in the system resulting in a high logic signal on hsw(k).

Figure 10:
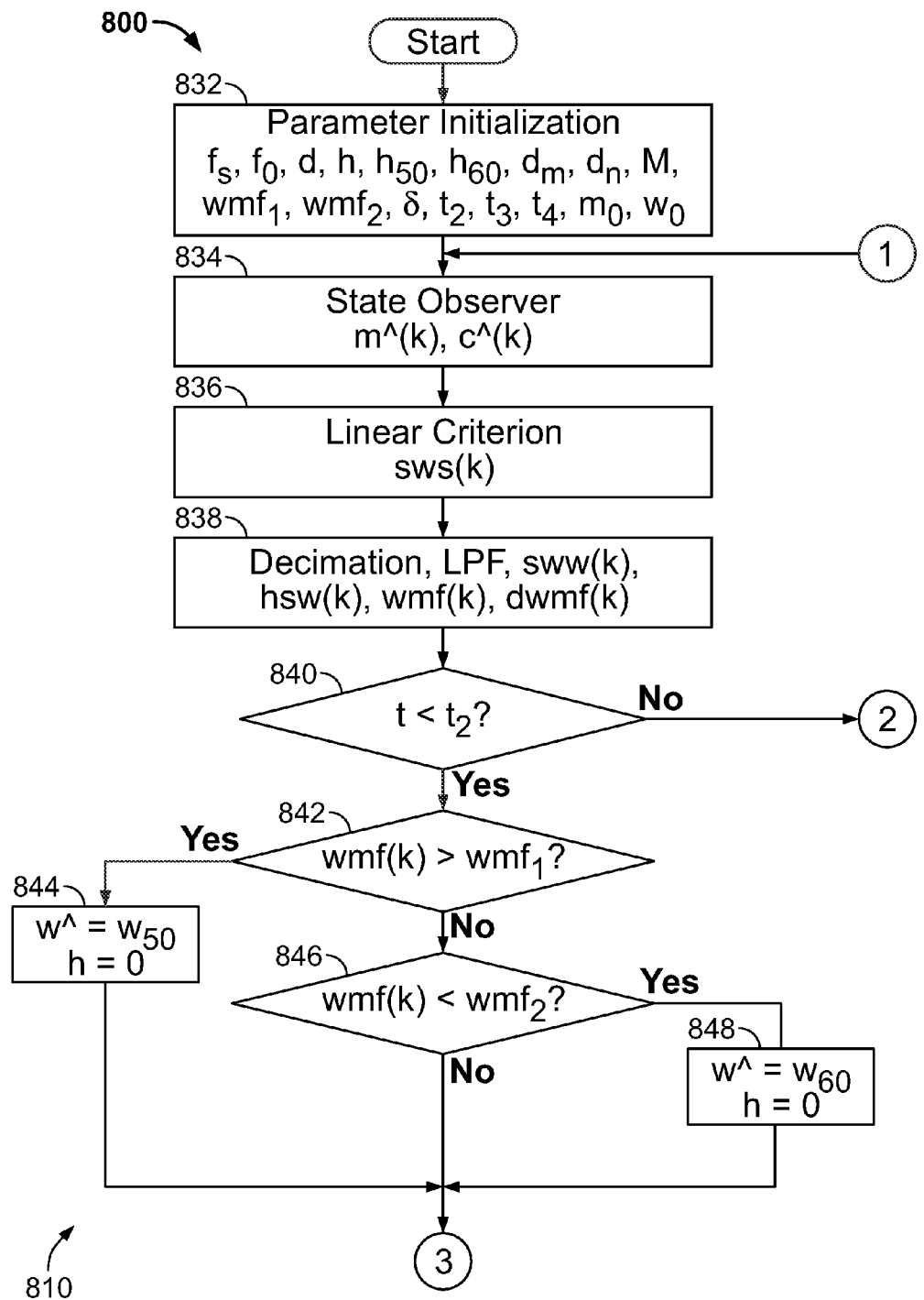
FIGS. 10-11 show flowcharts of a method by which adaptive notch filtration can be performed, according to an example embodiment.
Figure 11:
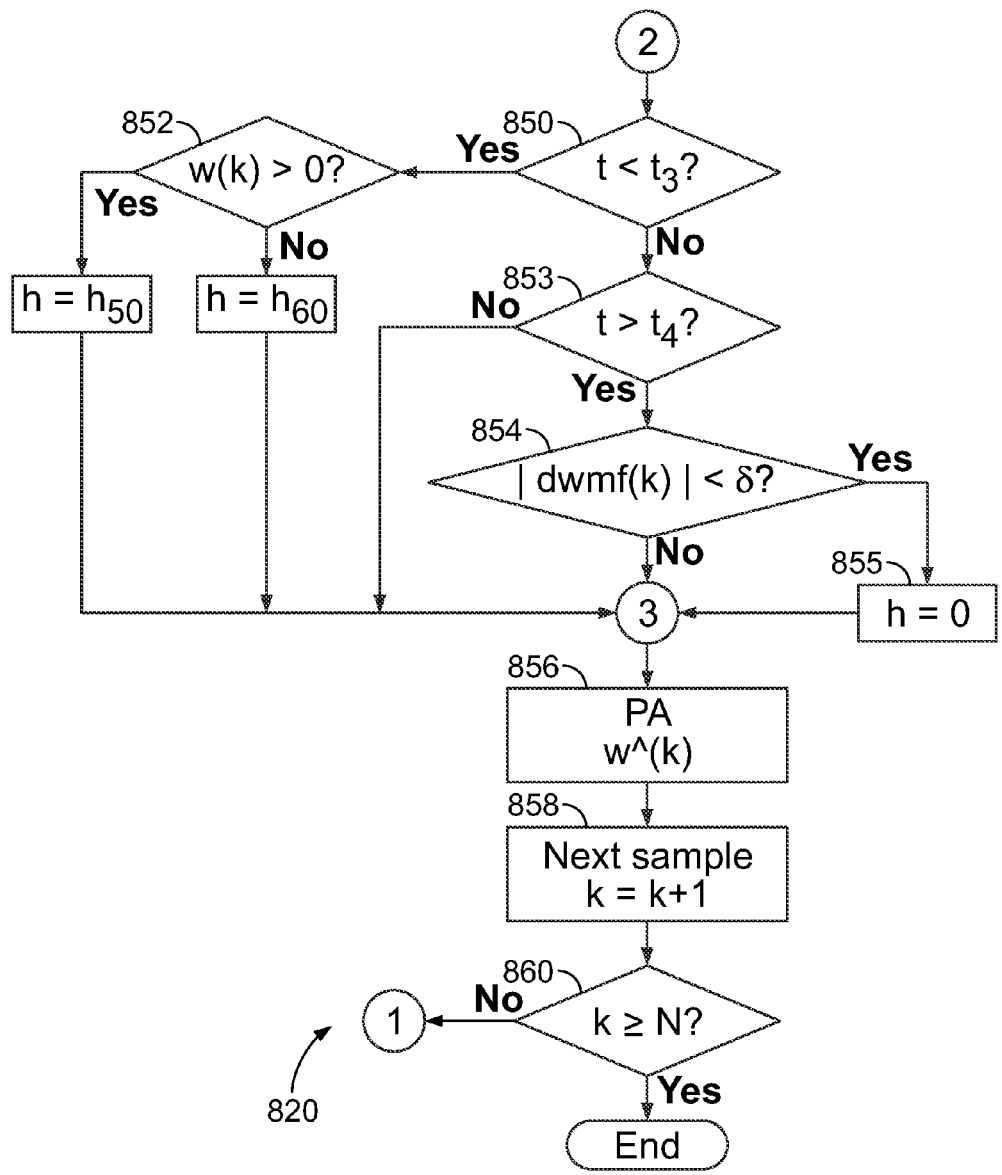

Referring now to FIGS. 10-11, flowcharts illustrating an overall method 800 for adaptation and filtration of a noisy signal, such as an ECG signal as interfered with via power line network, are disclosed. As illustrated in these figures, the system adaptation method generally includes two stages: a first frequency identification stage 810, and a second frequency adaptation stage 820.

In the embodiment shown, due to the fact that two widely used power line frequencies are 50 Hz and 60 Hz, the adaptation method 800 starts from an initial frequency parameter $w_0$ representing 55 Hz. the parameter adaptation will go towards two different directions for the two possible frequencies. With reference to FIG. 9, during time $0 \leq t \leq t_2$, the system is in the frequency identification stage 810. In particular, during the frequency identification stage, parameters are initialized as shown in Table 1 based on the 55 Hz assumption (step 832):

TABLE 1

Used Parameters

| Symbol | Parameter | Value | Unit |
|---|---|---|---|
| $f_s$ | sampling frequency | 500 | Hz |
| $f_0$ | initial frequency | 55 | Hz |
| d | error clamp | $1 \times 10^{-3}$ | |
| h | parameter update speed factor in frequency identification | 5 | |
| $h_{50}$ | parameter update speed factor in frequency adaptation when baseline frequency is 50 Hz | 5 | |
| $h_{60}$ | parameter update speed factor in frequency adaptation when baseline frequency is 60 Hz | 8 | |
| $d_m$ | decimation factor in RE | 50 | |
| $d_n$ | FD factor in RE | 50 | |
| M | CR threshold in RE | 0.15 | |
| $wmf_1$ | upper limit of wmf (k) in RE | 0.02 | |
| $wmf_2$ | lower limit of wmf (k) in RE | −0.02 | |
| δ | wmf (k) change rate threshold in RE | $2 \times 10^{-4}$ | |
| $t_2$ | time 2 | 3 | s |
| $t_3$ | time 3 | 4 | s |
| $t_4$ | time 4 | 5 | s |
| $m_0$ | initial value of noise | $[0\ 0]^T$ | |
| $w_0$ | initial value of unknown parameter | $[0\ 0]^T$ | |

At this point, operation of the system is initiated (process flow point 1), indicating that the ECG machine has begun operation. A state observer obtains estimations of signals m(k) and c(k) according to the general process described above (step 834). A linear criterion sws(k) is then determined at the robustness enhancer unit 530 (step 836), and, over a longer period of time, a wide angle logical output sww(k) is generated as well, thereby generating an overall logical output from the robustness enhancer unit 530 based on sws(k), sww(k), and therefore hsw(k), thereby dictating times at which adaptation should take place (step 838).

If time $t_2$ has not yet been reached (as determined in step 840), the system determines whether wmf exceeds a first threshold (step 842); if so, this indicates that there is sufficient information to determine that the parameter update has moved toward the 50 Hz direction, an assignment operation sets a parameter $w_{50}$ (step 844), representing a 50 Hz signal is to be assigned. Alternately, a second assessment operation determines whether wmf is below a second predetermined wmf threshold, noted as $wmf_2$ (step 846), an assignment operation sets a parameter $w_{60}$ (step 848), representing a 60 Hz signal is to be assigned. At this point, frequency identification has completed. The selection of $t_2$ should ensure the frequency identification process to have sufficiently long time to complete.

Referring back to step 840, if time $t_2$ is reached, a frequency adaptation stage 820 is entered. In the frequency adaptation stage, the parameter update is restarted in the overall system to track frequency variation an assessment of whether $t_3$ has yet been reached is made (step 850). If so, a new value for h, being a rate of adaptation, is set to either $h_{50}$ or $h_{60}$ value according to w(k) is positive or negative for the baseline frequency is 50 Hz or 60 Hz respectively, from the h for frequency identification (step 852). At this point, execution point 3 is reached, which would also be reached upon assigning either of the $w_{50}$ or $w_{60}$ parameters.

If time $t_4$ is exceeded, the change rate of wmf(k) is assessed (step 854). If it is less than or equal to a specific delta value (i.e., |dwmf(k)|≤δ), the adaptation is therefore forced to stop to enhance system stable robustness, setting h to 0 (step 855). At this point, the parameter adaptation unit 520 receives all the inputs, and adapts the parameter representing the noise frequency based on the state observer unit 510 (step 856). A next sample is acquired (step 858), and an assessment operation (step 860) either returns the system to execution point 1, or terminates operation of the adaptive method.

Referring now to FIGS. 12-18 generally, various waveforms are illustrated that show adaptation of a system to an ECG signal having power line interference of various frequencies. The waveforms generally illustrate both the frequency identification and frequency adaptation portions of the overall process 800 described in connection with FIGS. 10-11, above. In each of the waveforms, various ones of IEC60601-2-51 ANE2000/50 Hz and ANE2000/60 Hz ECG data are used.

Figure 12A:
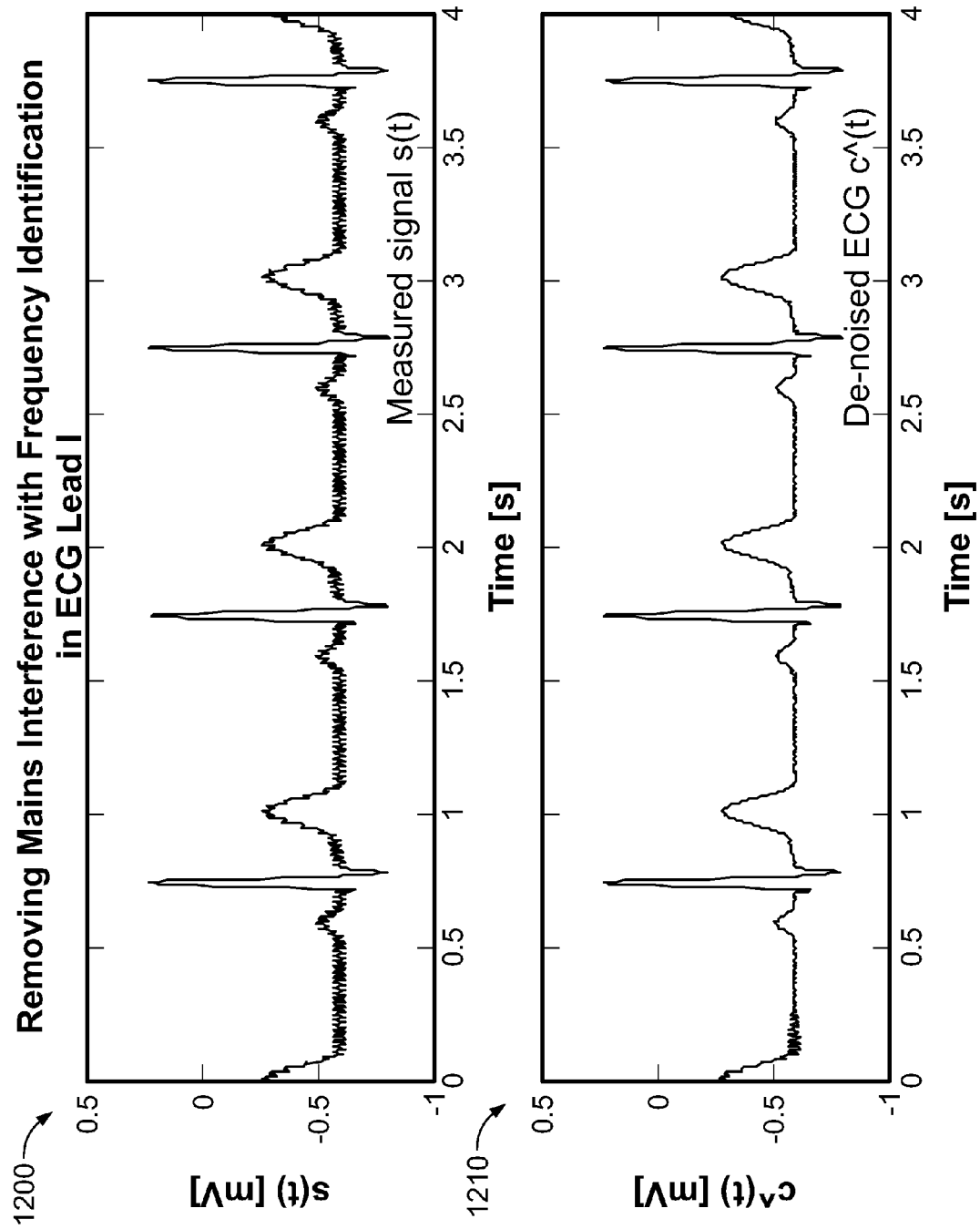
FIGS. 12a-c illustrate waveforms in simulation representing frequency identification using an example of the adaptive systems discussed herein, using a power line frequency of 50 Hz.
Figure 12B:
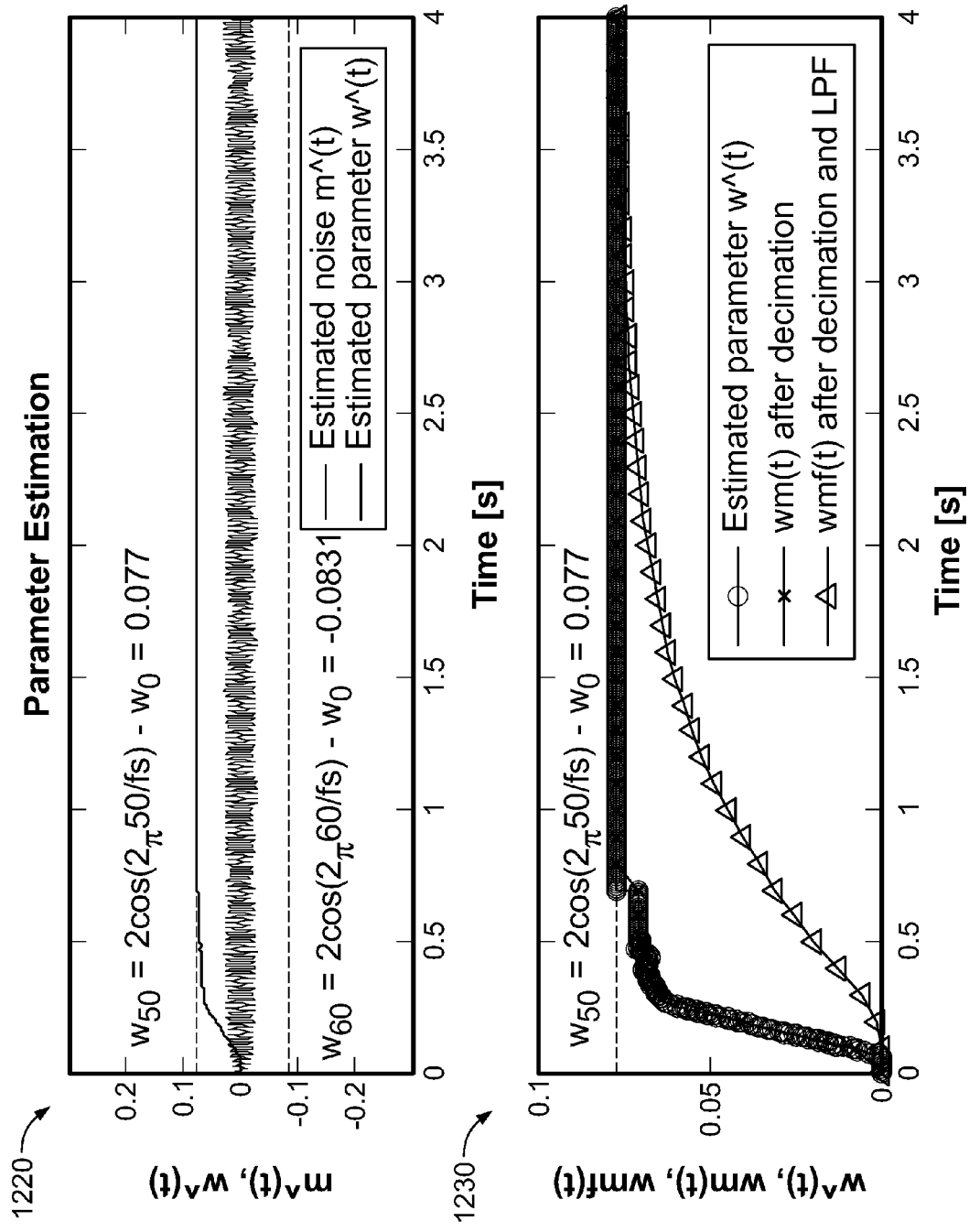
Figure 12C:
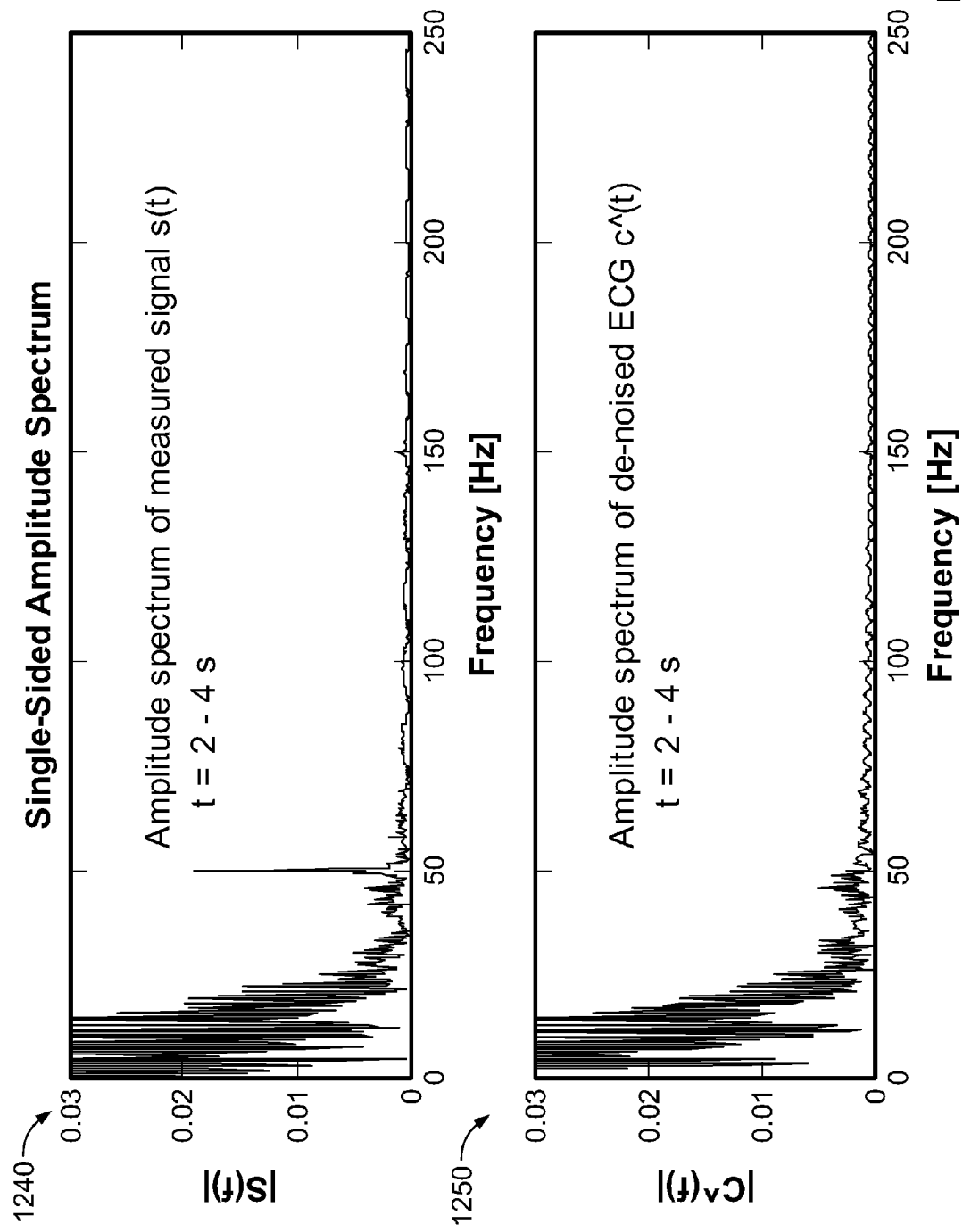

FIGS. 12*a-c* illustrate waveforms 1200, 1210, 1220, 1230, 1240. 1250 representing frequency identification using an example of the adaptive systems discussed herein, using a power line frequency of 50 Hz. Waveform 1210 of FIG. 12*a* shows that the noise is cancelled and the ECG signal is denoised, as compared to original signal 1200. Waveform 1220 of FIG. 12*b* shows that the estimated noise m̂(k) approaching the power line interference, the estimated frequency parameter ŵ(k) approaches its target value $w_{50}$. Waveform 1230 of FIG. 12*b* illustrates the parameter update process of ŵ(k) and the signal 614 after being processed by the decimation and low-pass filter in the robustness enhancer module 530. It can be seen that at around 0.7 s, the system learns that the parameter will be approaching 50 Hz, so it forces the parameter to 50 Hz and stops the update (i.e., as in step 844 of method 800). FIG. 12*c* demonstrates a fast Fourier transform based on observed data from 4 s onwards; the noise having a peak at 50 Hz in frequency spectrum 1240 (the unfiltered frequencies) is effectively removed, as seen in frequency spectrum 1250 (seen as the spike in S(f) at 50 Hz being removed).

Figure 13A:
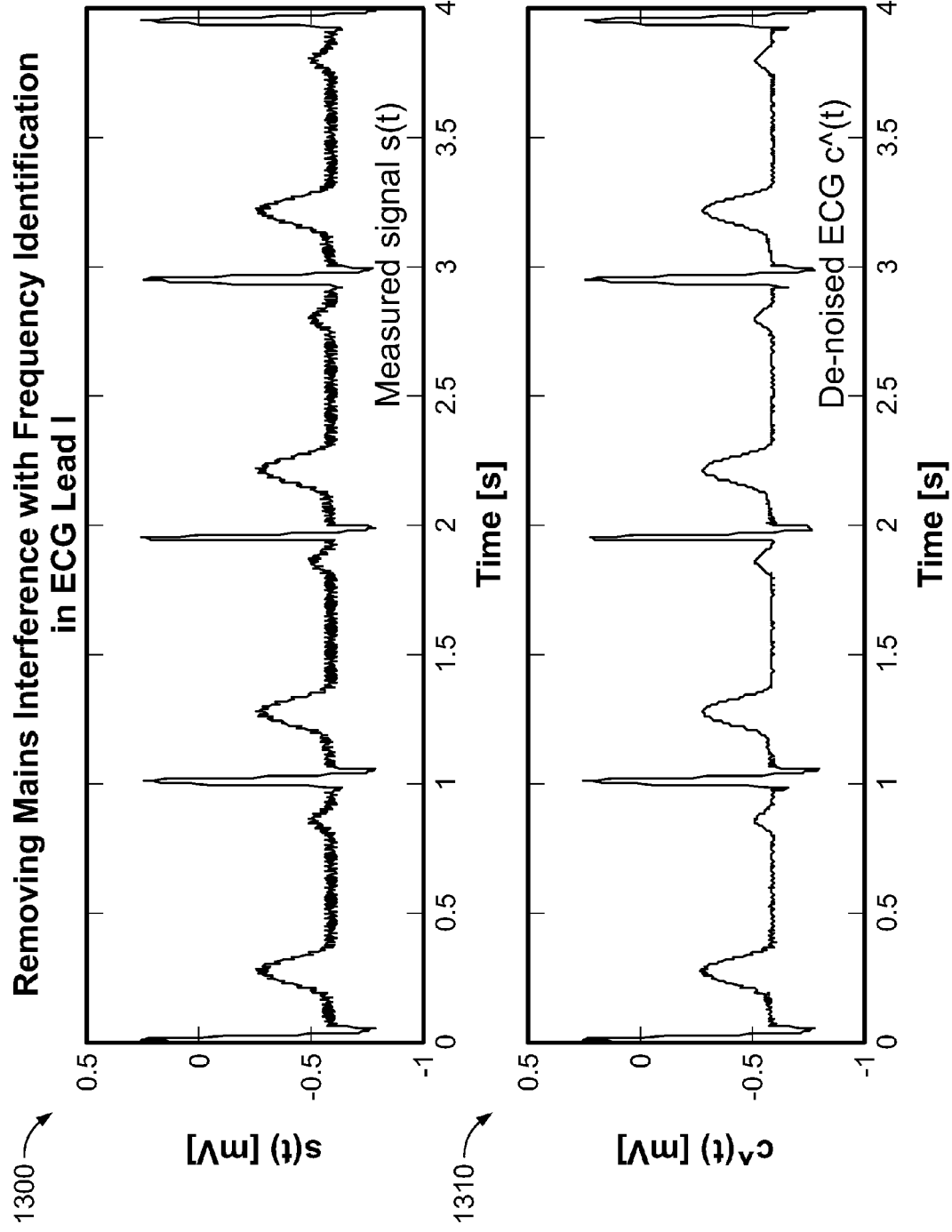
FIGS. 13a-c illustrate waveforms in simulation representing frequency identification using an example of the adaptive systems discussed herein, using a power line frequency of 60 Hz.
Figure 13B:
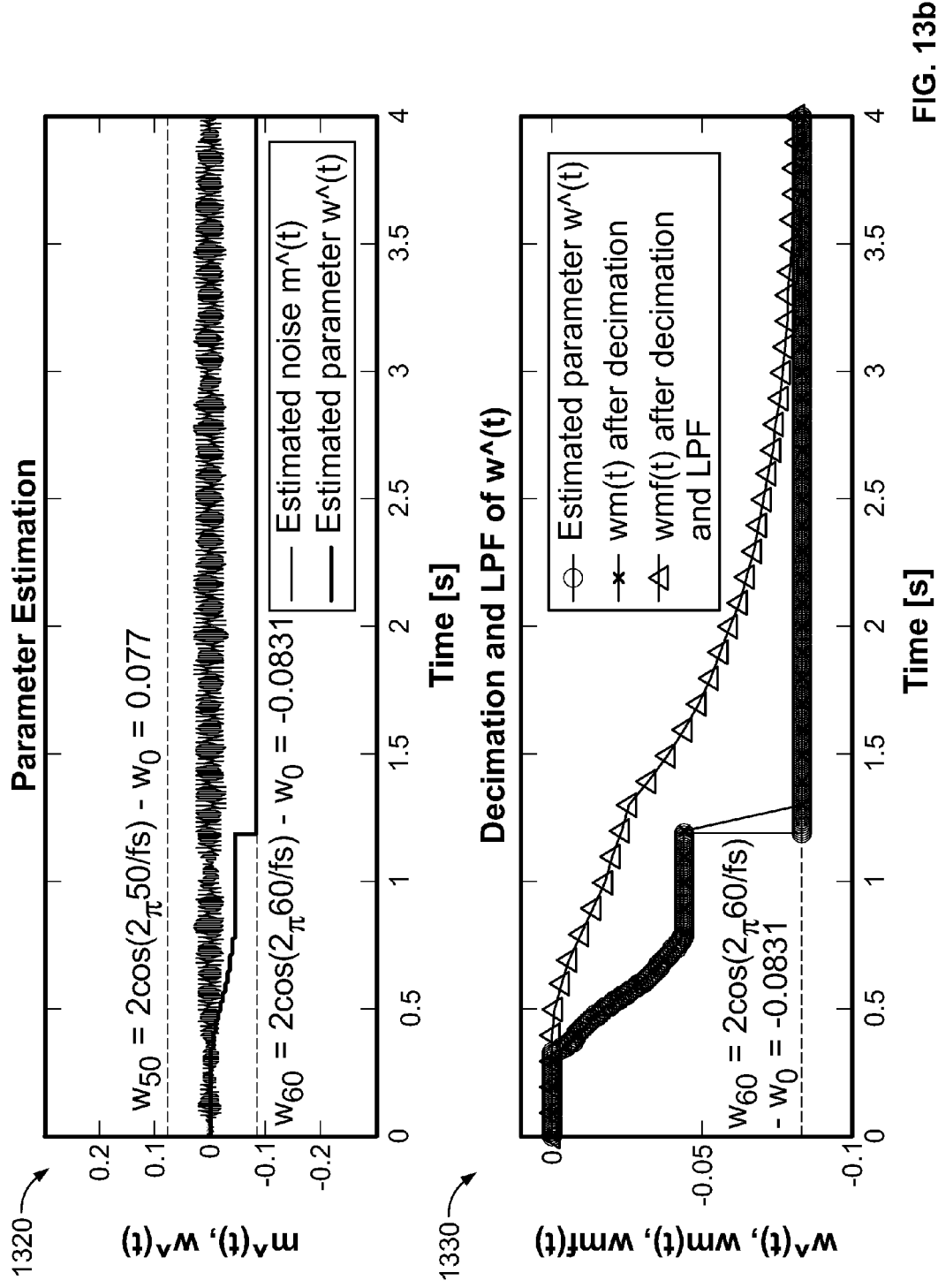
Figure 13C:
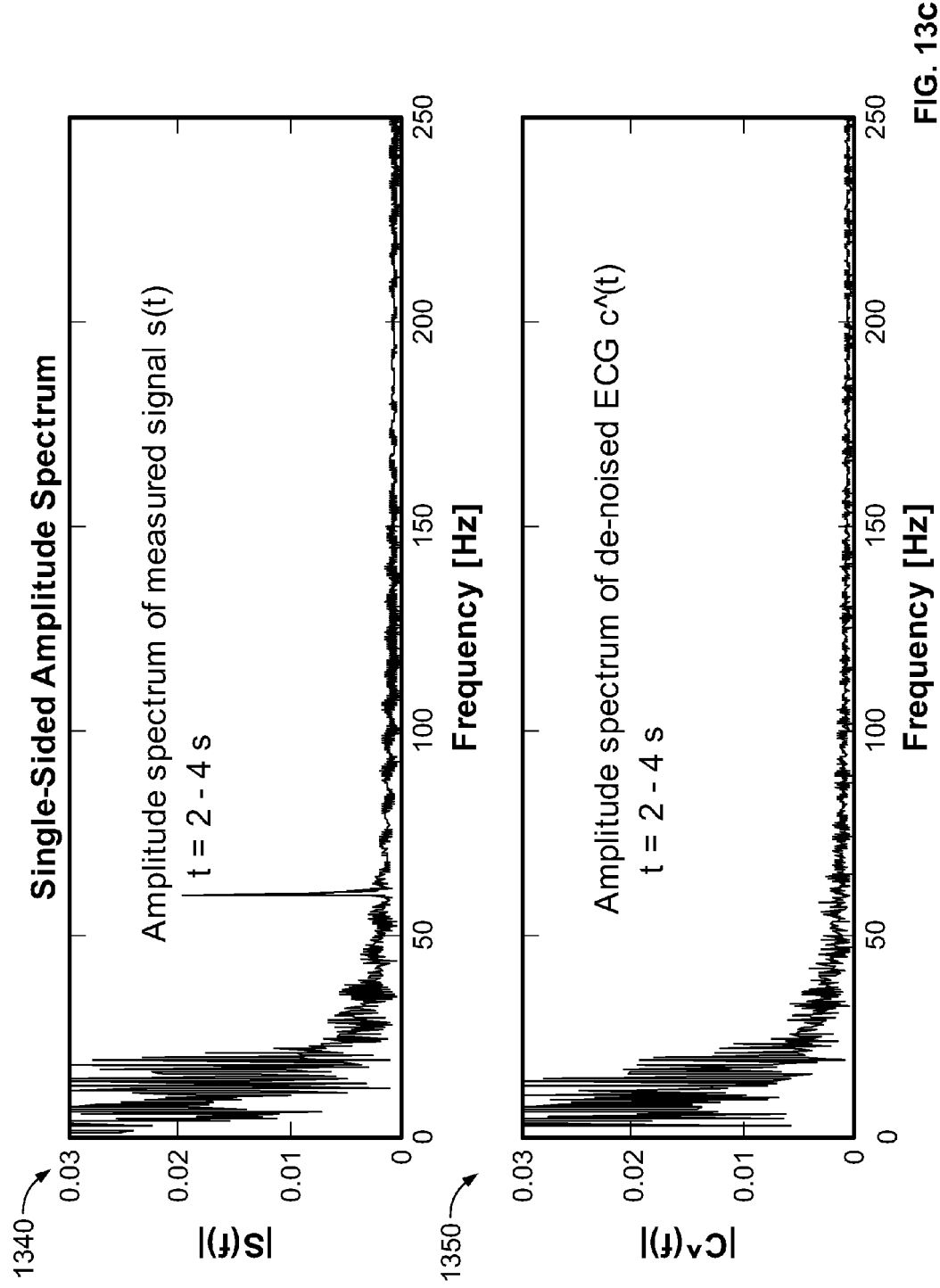
Figure 14A:
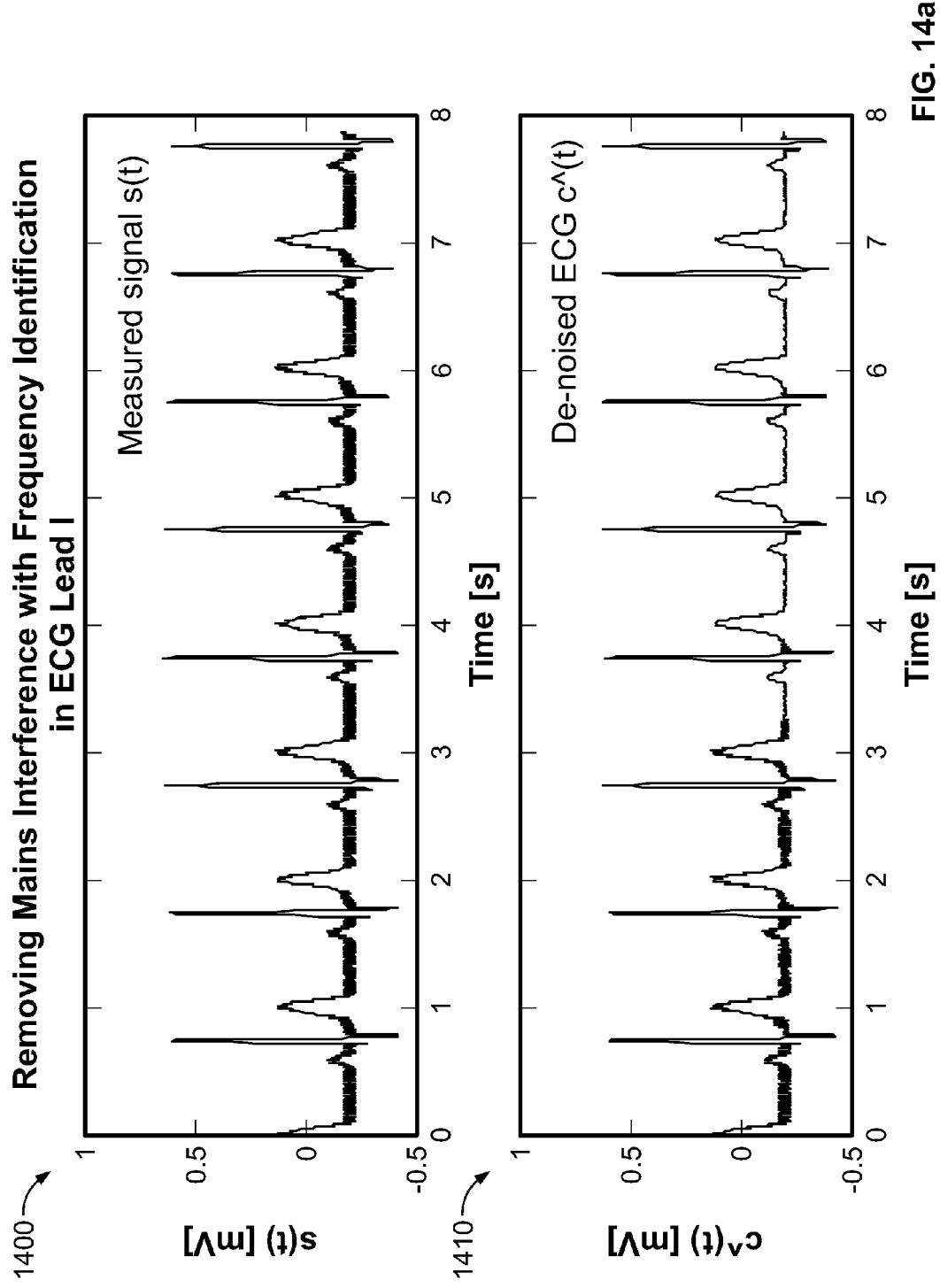
FIGS. 14a-c illustrate waveforms in simulation demonstrating the effectiveness of the frequency identification and frequency adaptation using an example of the adaptive systems discussed herein, by simulating frequency adaptation to 45 Hz (50−10% Hz).
Figure 14B:
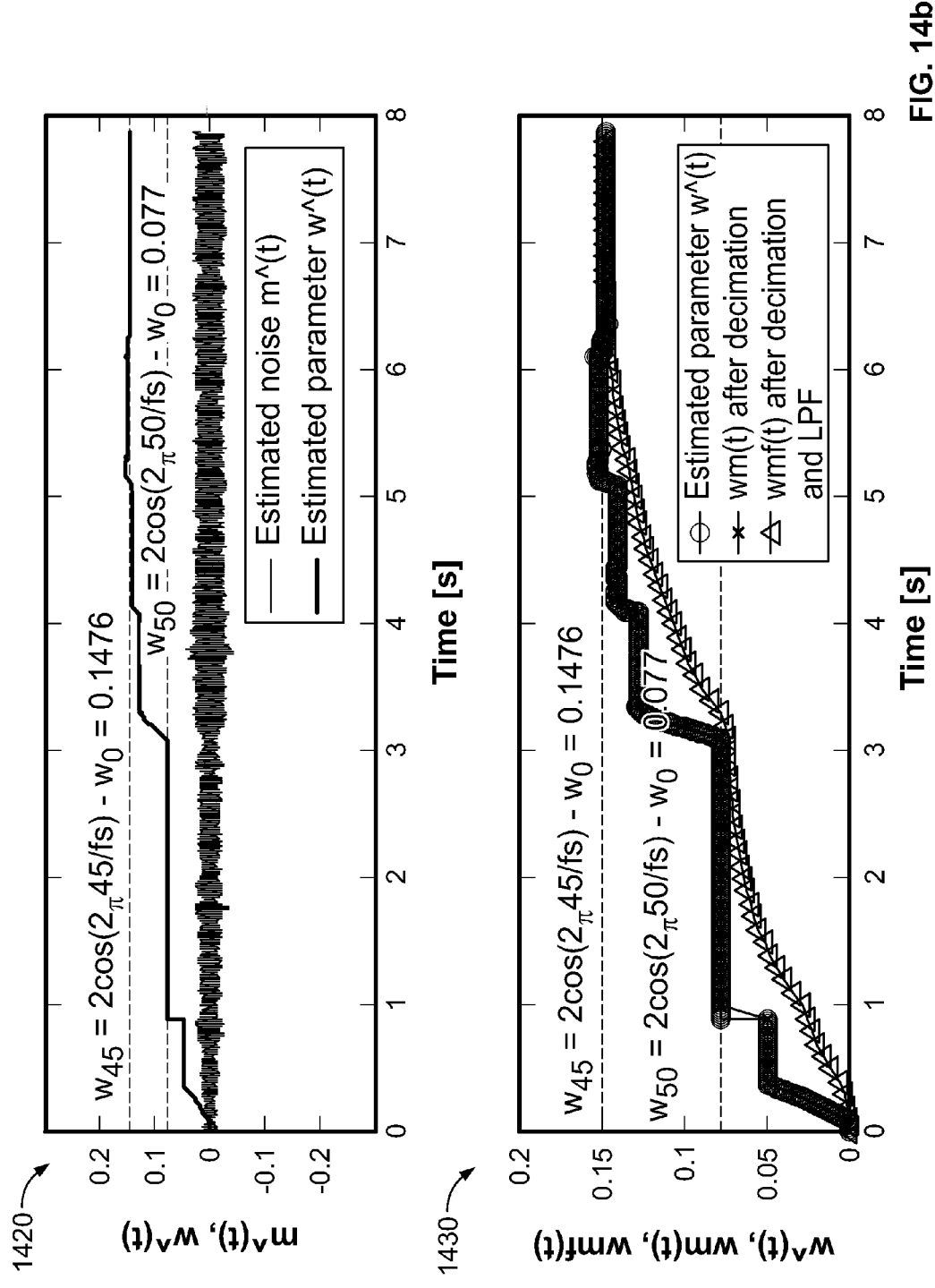
Figure 14C:
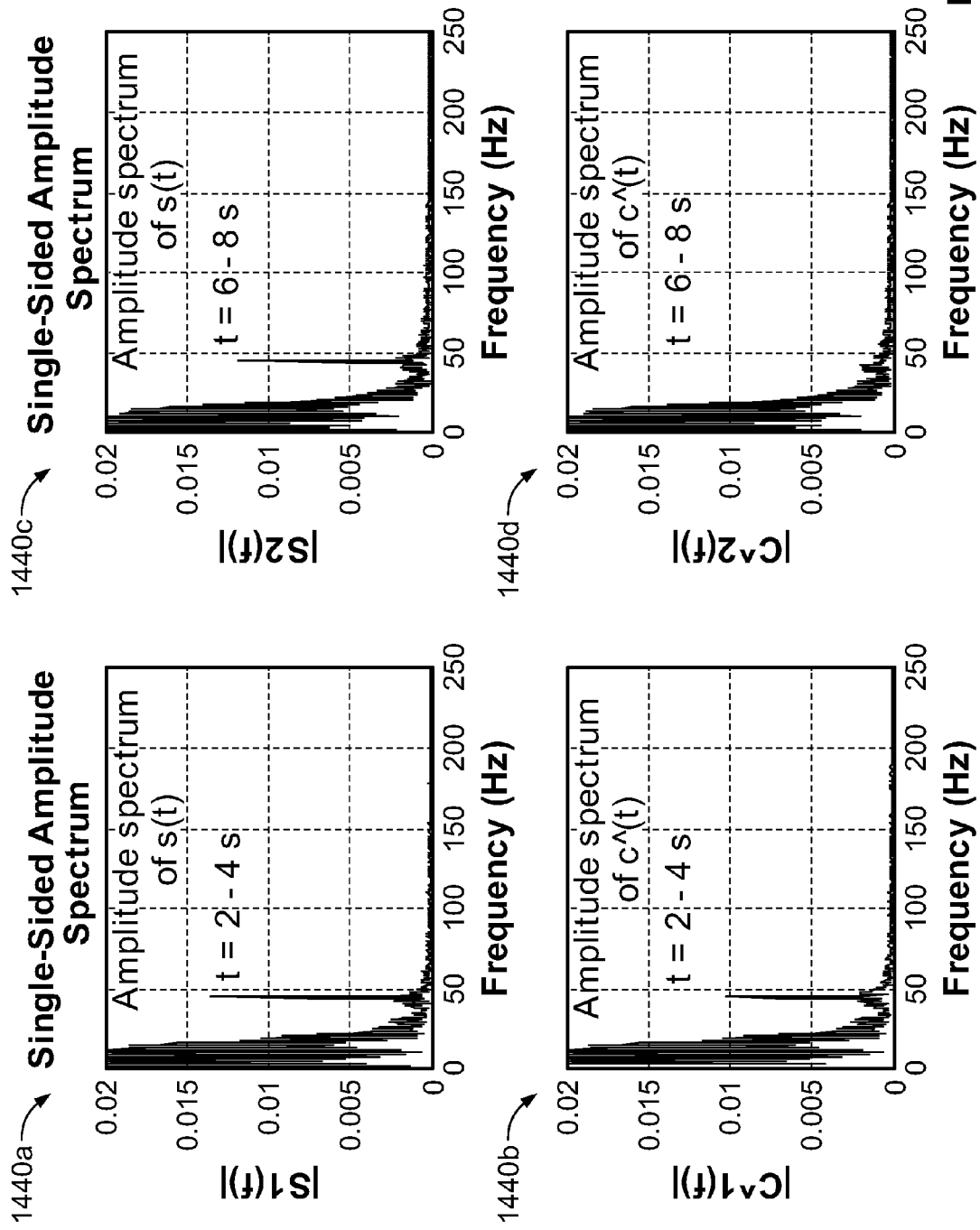

FIGS. 13*a-c* illustrate waveforms 1300, 1310, 1320, 1330, and frequency charts 1340, 1350 representing frequency identification using an example of the adaptive systems discussed herein, using a power line frequency of 60 Hz. These waveforms 1300, 1310, 1320, 1330, 1340, 1350 are generally analogous to those illustrated in FIGS. 12*a-c*, but due to the fact that a 60 Hz power signal is used, a spike shown in FIG. 13*c* is at 60 Hz rather than at 50 Hz. In this case, and as seen in FIG. 13*b*, the parameter update stops at around 1.3 s.

FIG. 14-17 show examples where both frequency identification and frequency adaptation phases are applied, from method 800. FIGS. 14*a-c* illustrate waveforms 1400, 1410, 1420, 1430, and 1440*a-d* demonstrating the effectiveness of the frequency identification using an example of the adaptive systems discussed herein, by simulating frequency adaptation to 45 Hz (50-10% Hz). In this example, a frequency identification stage occurs within 3 s, but the entire noise is not canceled since the identified frequency is initially 50 Hz (assigned at about 1.5 s). In this case, the noise frequency is assigned to 50 Hz at around 1.5 s. A frequency adaptation stage starts at about 3 s and the parameter approaches its target value of 45 Hz (see waveforms 1420, 1430 of FIG. 14*b*). As a result, the noise is cancelled (see waveform 1410 of FIG. 14*a*, waveforms 1420, 1430 of FIG. 14*b*). In FIG. 14*c*, frequency graphs 1440*a-d* show the FFT based on the data from 4 s onwards, with the noise effectively eliminated at 45 Hz (i.e., the S(f) peak at 45 Hz is shown as eliminated after about 6-8 seconds, in frequency graph 1440*d*).

Figure 15A:
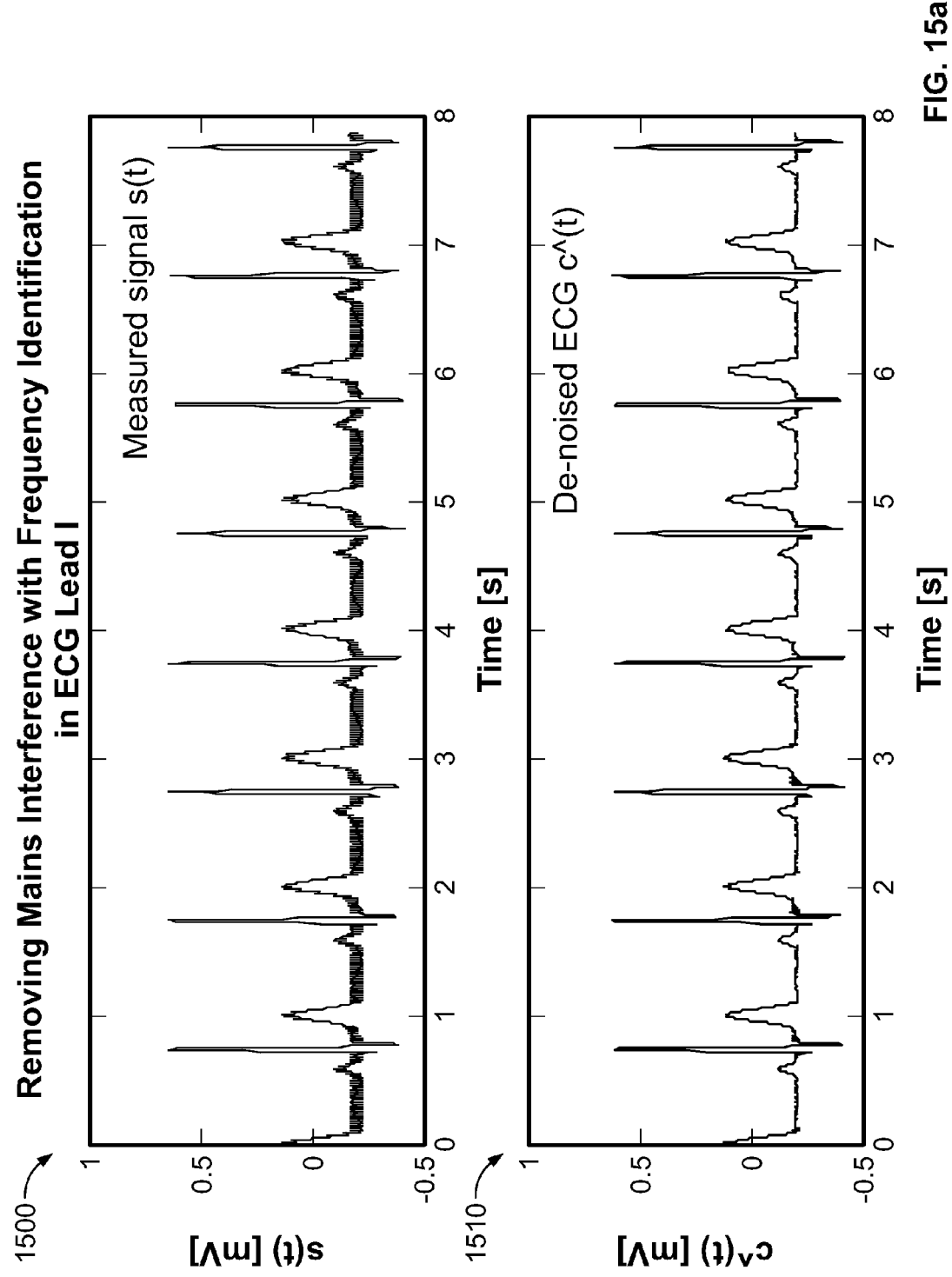
FIGS. 15a-c illustrate waveforms in simulation demonstrating the effectiveness of the frequency identification and frequency adaptation using an example of the adaptive systems discussed herein, by simulating frequency adaptation to 52 Hz (50+4% Hz).
Figure 15B:
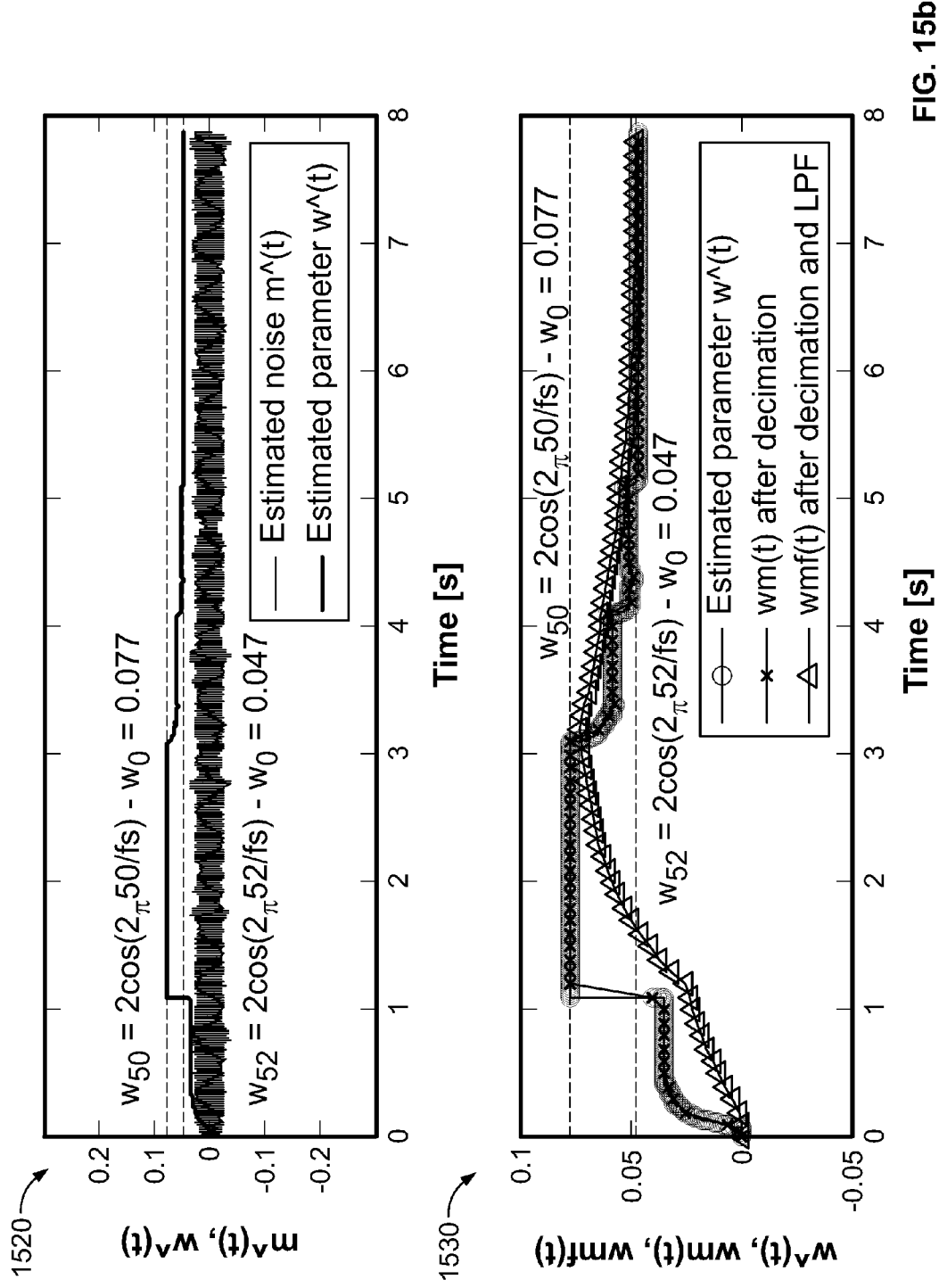
Figure 15C:
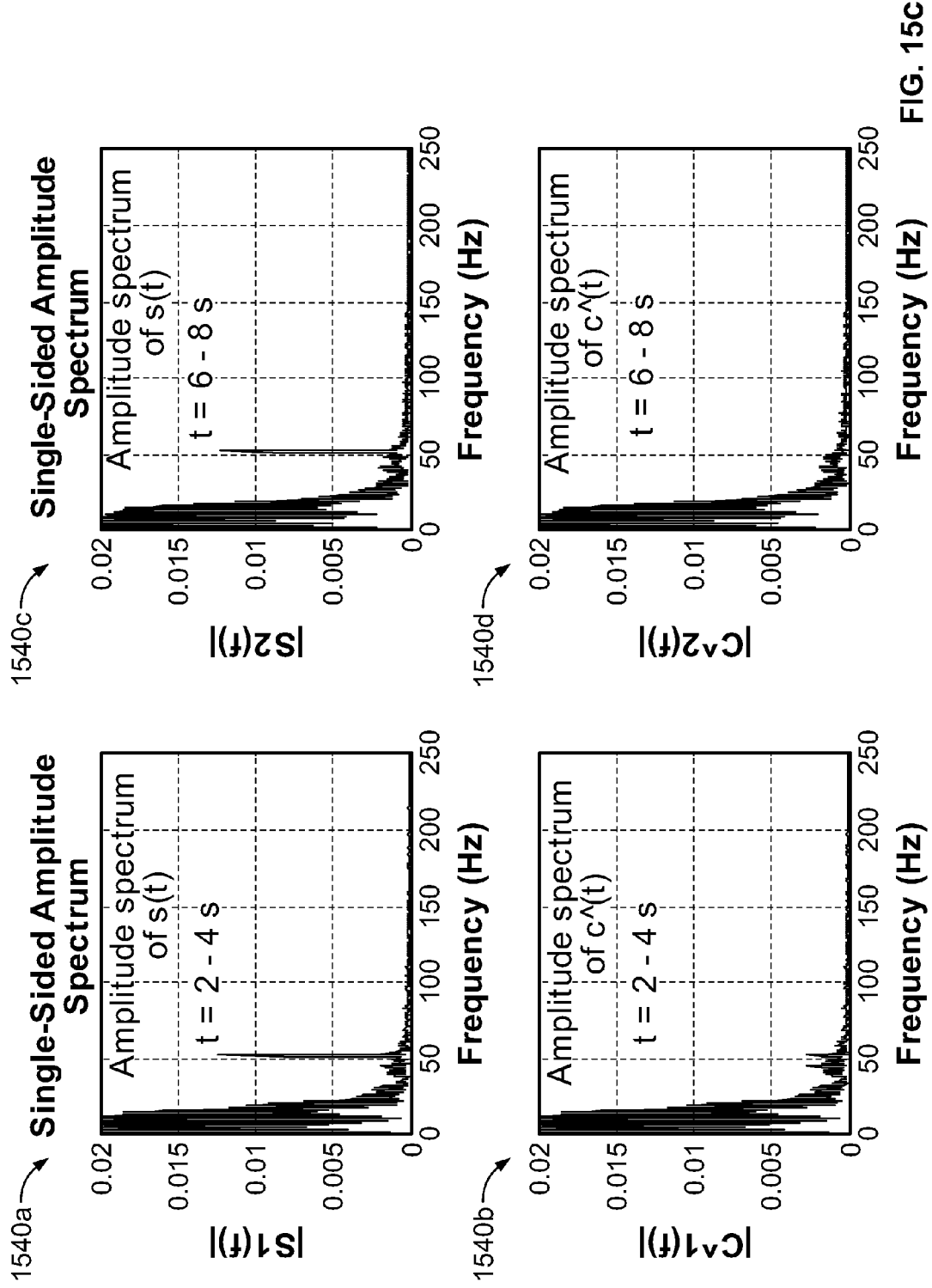

FIGS. 15*a-c* illustrate waveforms 1500, 1510, 1520, 1530, and frequency charts 1540*a-d* demonstrating the effectiveness of the frequency identification and frequency adaptation using an example of the adaptive systems discussed herein, by simulating frequency adaptation to 52 Hz (50+4% Hz). In this case, frequency is set to 50 Hz in the frequency identification stage, and adapted to 52 Hz during the frequency adaptation phase, settling after about 5 s (see particularly waveform 1530 of FIG. 15*b*, and comparing frequency chart 1540*c-d*).

Figure 16A:
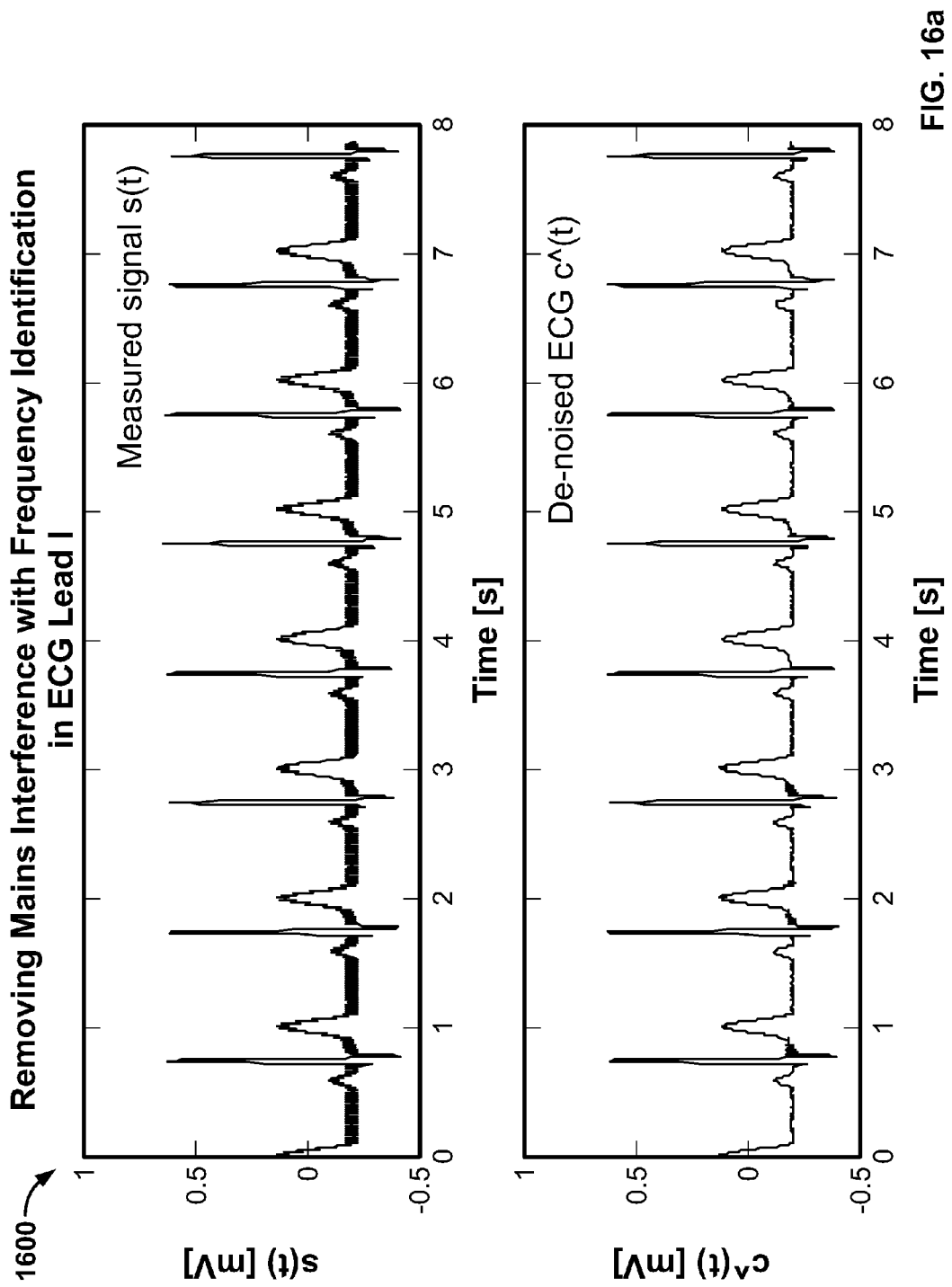
FIGS. 16a-c illustrate waveforms in simulation demonstrating the effectiveness of the frequency identification and frequency adaptation using an example of the adaptive systems discussed herein, by simulation frequency adaptation to 58 Hz (60−3.3% Hz).
Figure 16B:
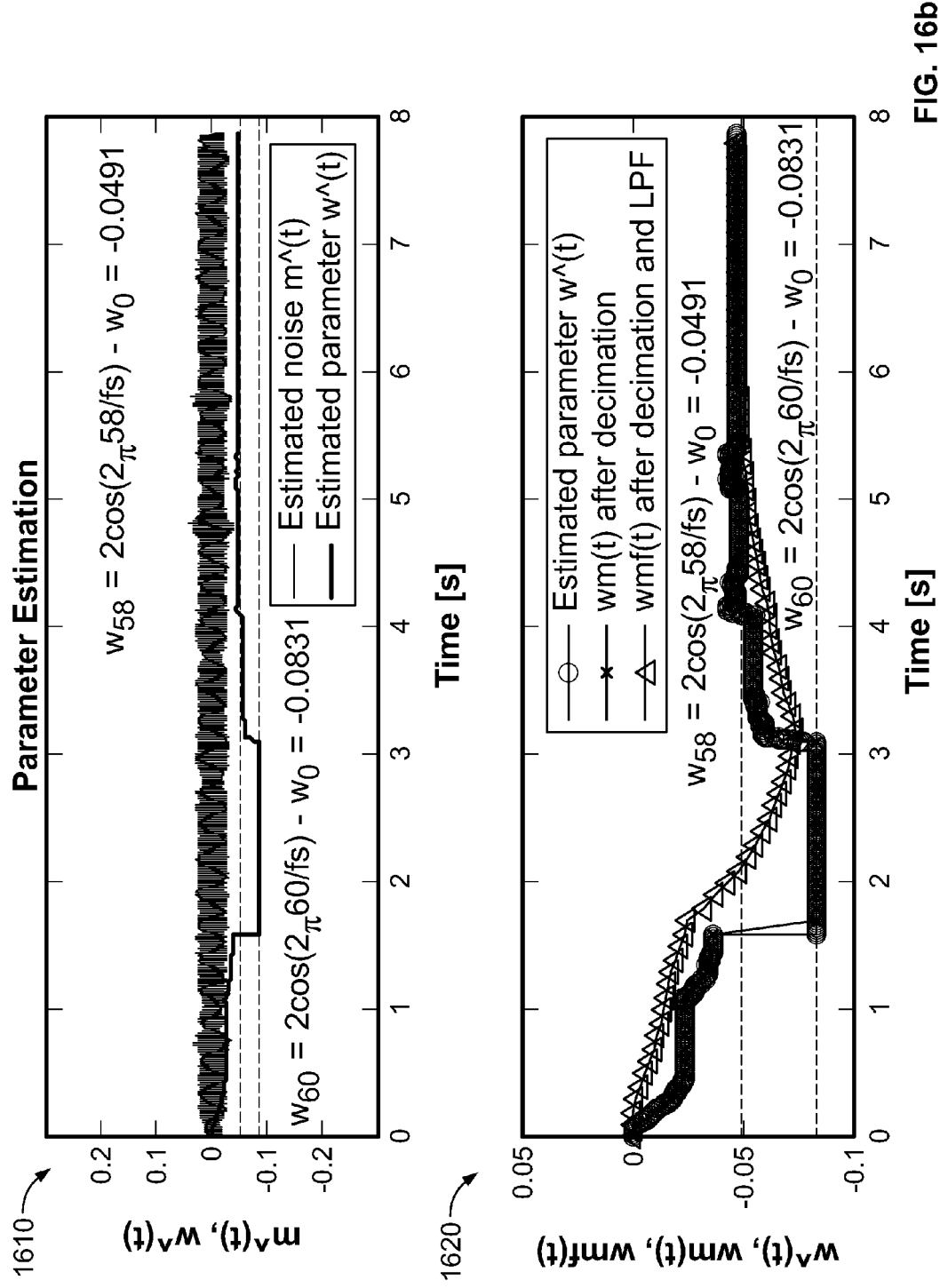
Figure 16C:
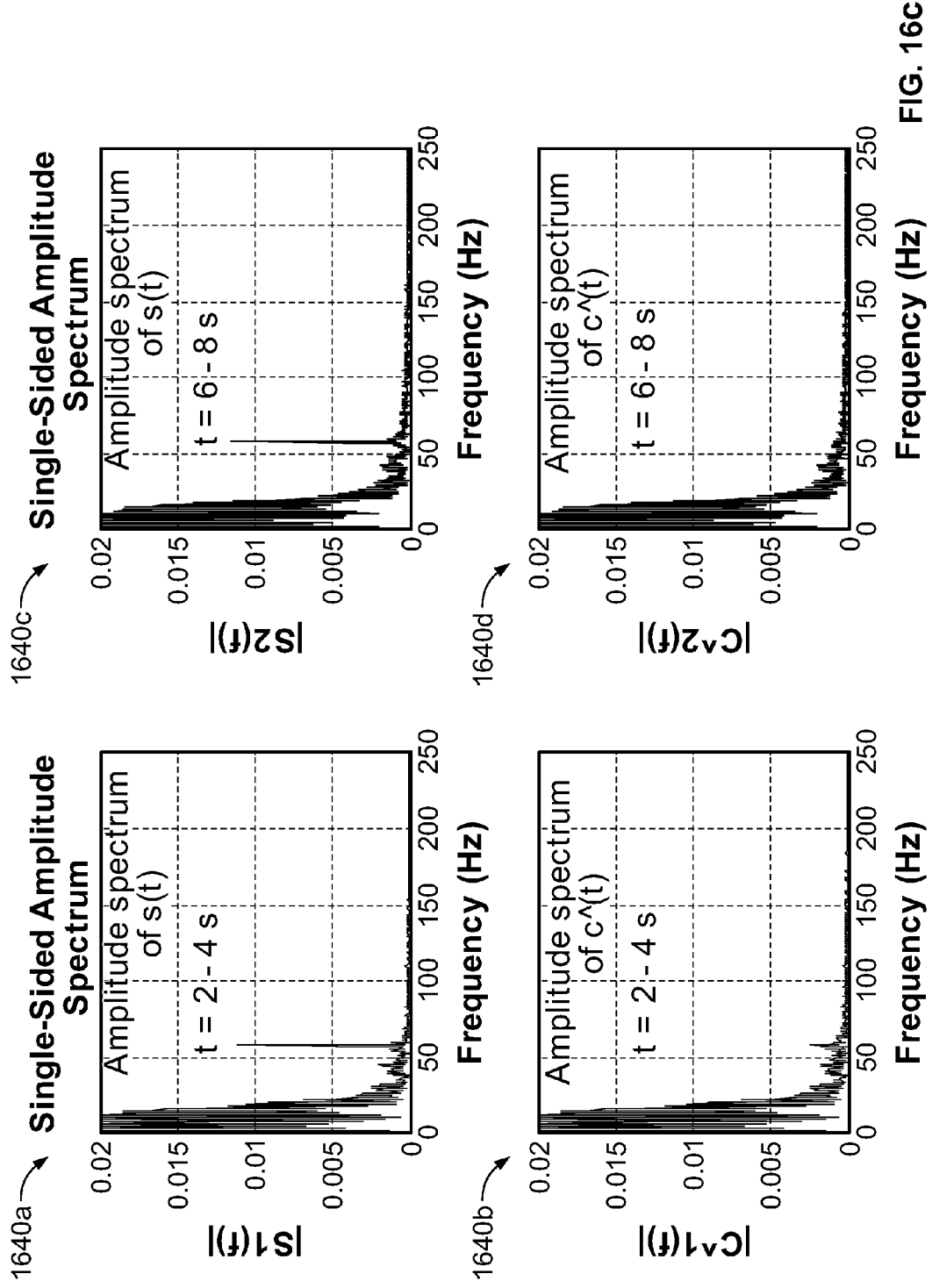

FIGS. 16*a-c* illustrate waveforms 1600, 1610, 1620, 1630, and frequency charts 1640*a-d* demonstrating the effectiveness of the frequency identification and frequency adaptation using an example of the adaptive systems discussed herein, by simulation frequency adaptation to 58 Hz (60-3.3% Hz). In this case, frequency is set to 60 Hz in the frequency identification stage (at about 1.5 s, in waveform 1620 of FIG. 16*b*) and after about 3 s, the frequency adaptation stage adapts to 58 Hz (seen in waveform 1630 of FIG. 15*b* and a comparison of frequency charts 1640*c-d* of FIG. 16*c*).

Figure 17A:
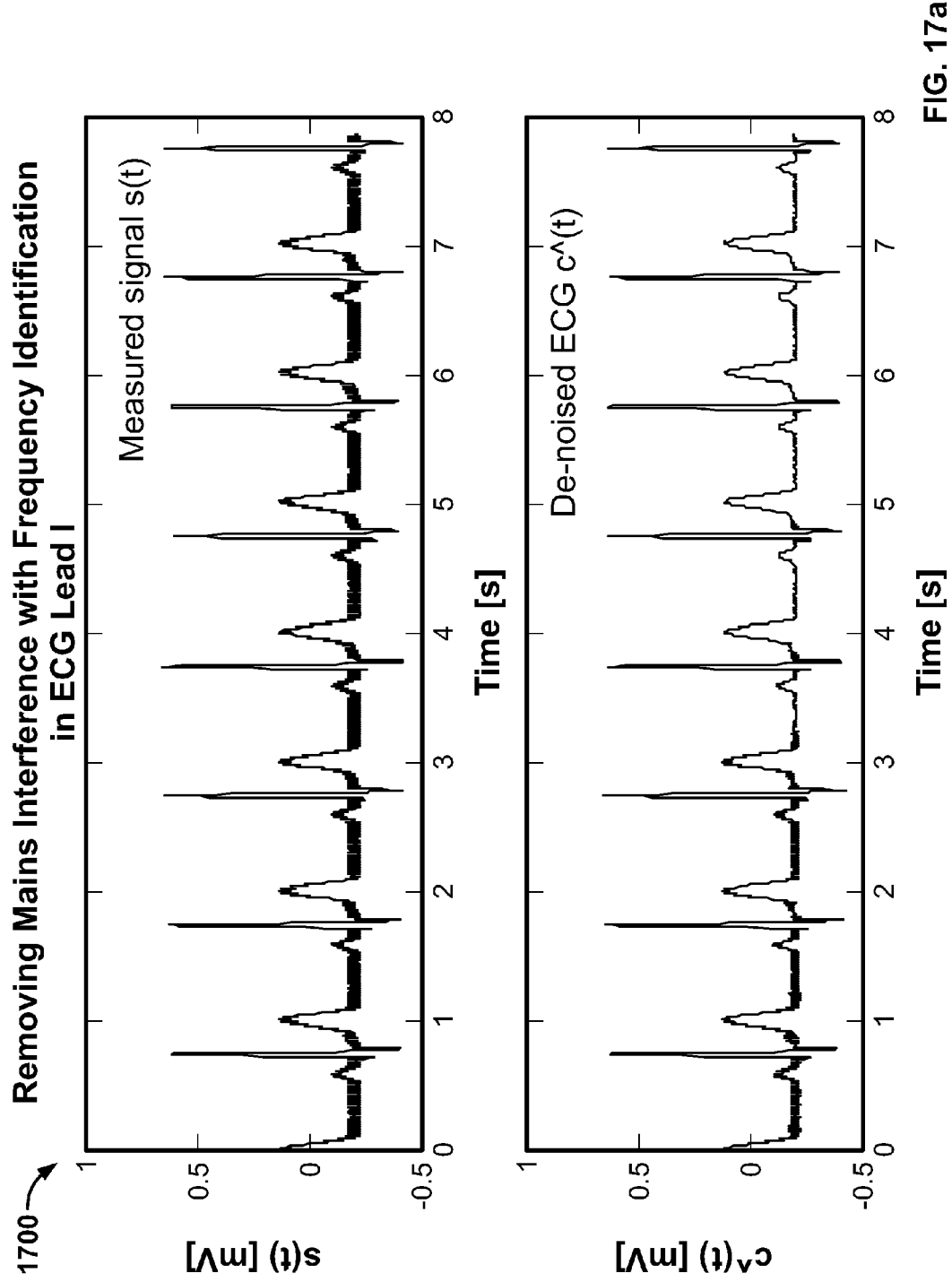
FIGS. 17a-c illustrate waveforms in simulation demonstrating the effectiveness of the frequency identification and frequency adaptation using an example of the adaptive systems discussed herein, by simulation frequency adaptation to 65 Hz (60+8.3% Hz).
Figure 17B:
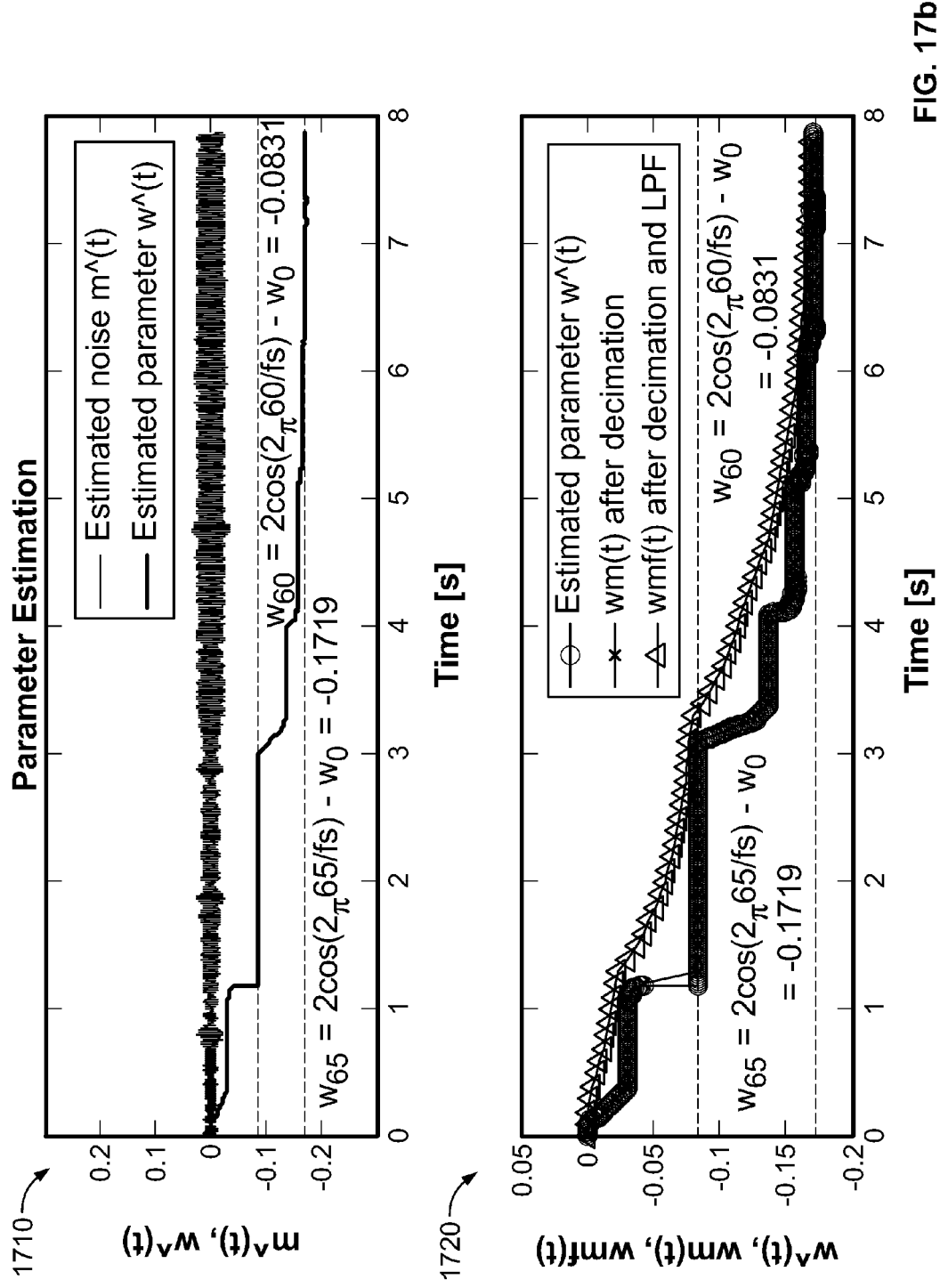
Figure 17C:
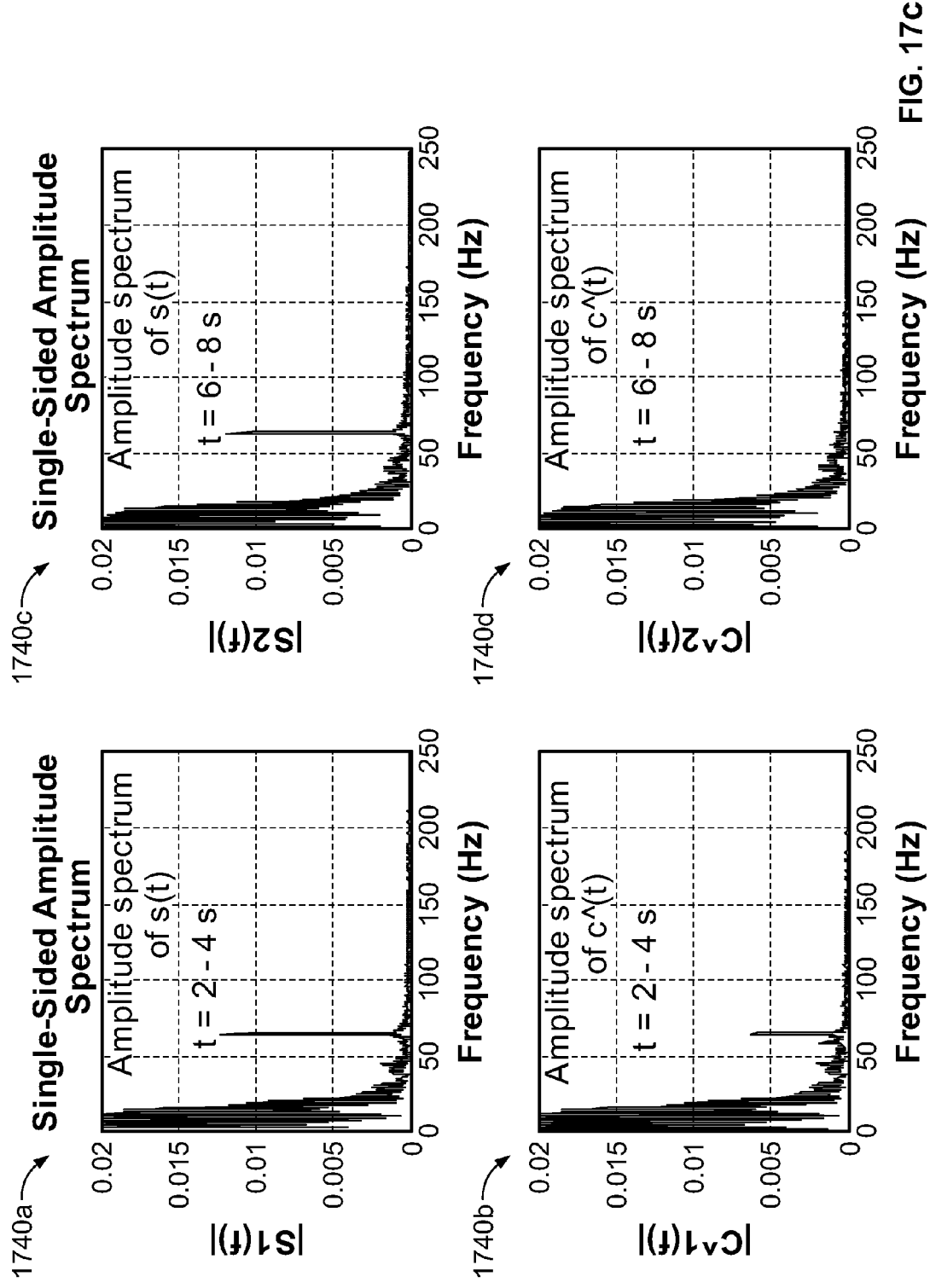

FIGS. 17*a-c* illustrate waveforms 1700, 1710, 1720, 1730, and frequency charts 1740*a-d* demonstrating the effectiveness of the frequency identification and frequency adaptation using an example of the adaptive systems discussed herein, by simulation frequency adaptation to 65 Hz (60+8.3% Hz). Again, during frequency identification the frequency is set to 60 Hz within about 3 s of operation, and frequency adaptation causes adjustment to 65 Hz within about 6-7 s.

Figure 18A:
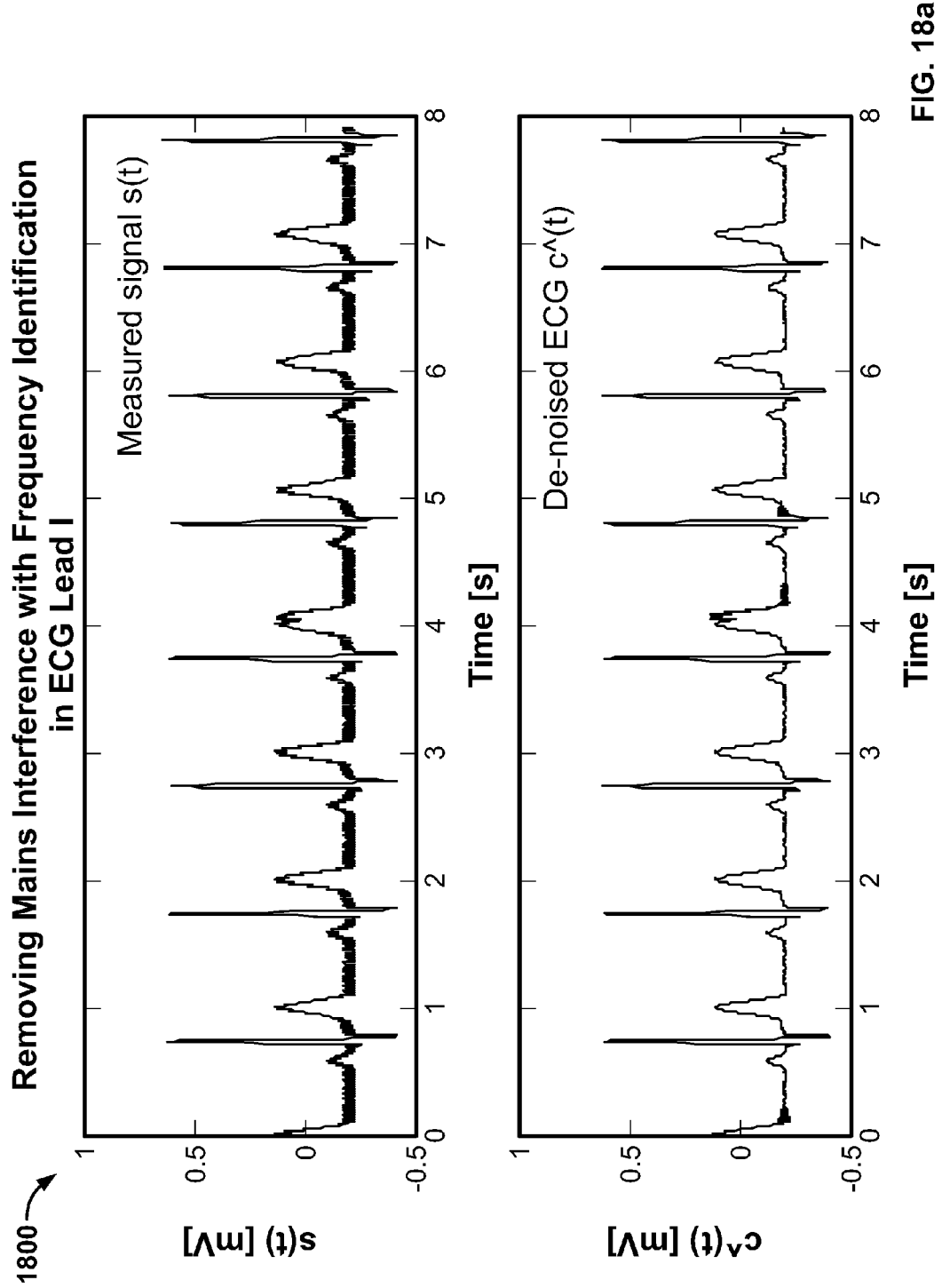
FIGS. 18a-c illustrate waveforms in simulation demonstrating the effectiveness of the frequency identification and frequency adaptation using an example of the adaptive systems discussed herein, by simulation in which frequency changes from 50 Hz to 45 Hz.
Figure 18B:
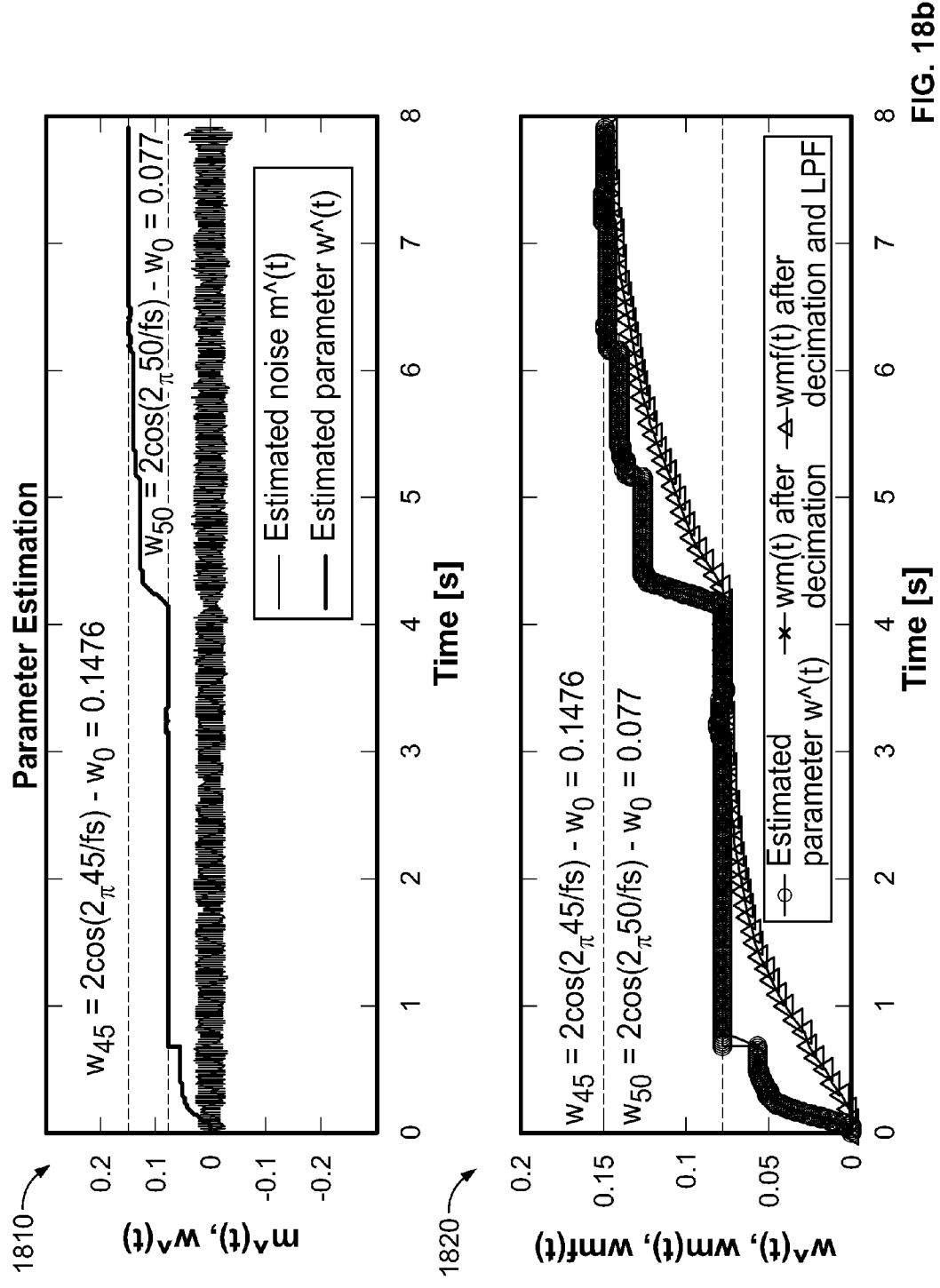
Figure 18C:
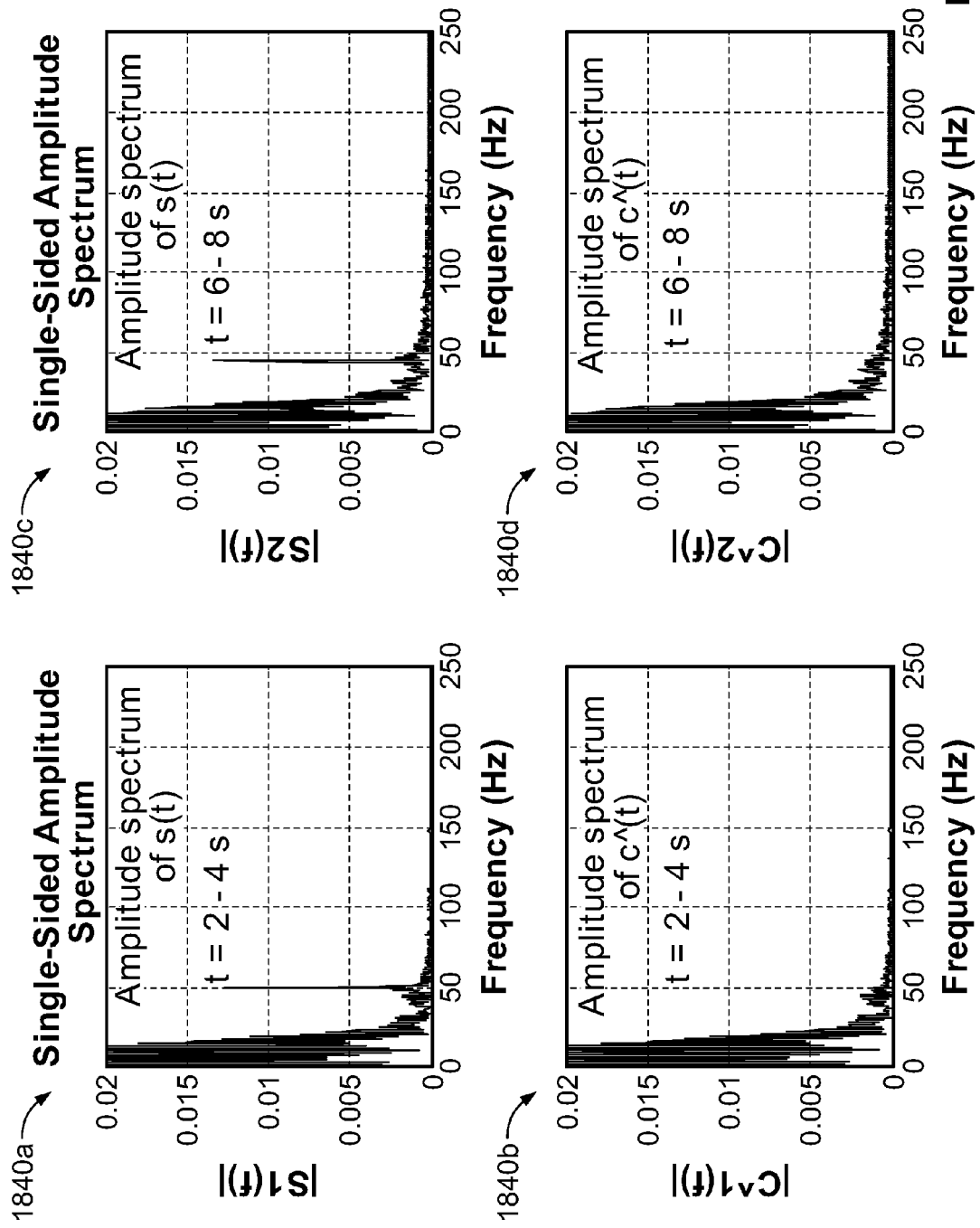

FIGS. 18*a-c* illustrate waveforms 1800, 1810, 1820, 1830, and frequency charts 1840*a-d* demonstrating the effectiveness of the frequency identification and frequency adaptation using an example of the adaptive systems discussed herein, by simulation in which frequency changes from 50 Hz to 45 Hz. In this case, frequency adaptation occurs on a 50 Hz signal at about 3 s, but a power line source frequency changes at about 4 s. In this case, it can be seen that the adaptation phase recognizes and adapts to the new 45 Hz frequency (with frequency charts 1840*a-d* of FIG. 18*c* showing noise at both 50 Hz and 45 Hz frequencies each being filtered).

Referring to FIGS. 1-18 overall, it is noted that the methods and apparatus for removing sinusoidal noise with unknown and time-varying frequency, can be adapted to a variety of different expected frequencies, and can thereby adapt to particular frequencies as needed. In accordance with the apparatus and methods described herein it is noted that, using the adaptive notch-filtering described herein it is possible to eliminate sinusoidal noise, in particular, to remove the interference in ECG measurement due to power line network interference even when the frequency of that interference is unknown and varying over time. As noted, due to the adaptability of the system, an apparatus constructed according to the principles discussed herein can adapt to differing power line frequencies without requiring user knowledge of the power line frequency or input into the device, and is constructed to automatically remove the power line interference as the notch filter and associated ECG machine is being turned on.

Furthermore, although the above illustration provides an example implementation of the frequency identifying and adaptive notch filter of the present disclosure, it is noted that many variations may exist which are consistent with and encompassed by the concepts disclosed herein. For example, in some embodiments, only a portion of the disclosed systems might be used. In such an example, it may be the case that only a frequency identification portion is implemented, without attendant adaptation of a filter. In still other embodiments, an alternative robustness enhancer unit can be employed that applies a different type or extent of robustness analysis. In further embodiments, a robustness enhancer unit can be excluded from a system altogether.

In some embodiments, the present disclosure can further be used to eliminate higher order harmonic signals. For example, second and third harmonics of a noise signal can be captured, for example by either recalling subroutines relating to harmonic detection, or by expanding a parameter matrix in the observer. In particular, based on the fact that $\cos nx = 2\cos x \cdot \cos(n-1)x - \cos(n-2)$, it yields $$\begin{cases} \cos 2x = 2\cos^2 x - 1, \\ \cos 3x = 4\cos^3 x - 3\cos x \end{cases}.$$

If the parameters representing the unknown frequencies of the fundamental component $\hat{f}_n$, the second harmonic component $2\hat{f}_n$ and the third harmonic component $3\hat{f}_n$ are denoted as $\hat{w}_1$, $\hat{w}_2$, and $\hat{w}_3$ respectively, then for $\hat{w}_1 = 2\cos(2\pi \hat{f}_n/f_s)$, we have $$\begin{cases} \hat{w}_2 = \hat{w}_1^2 - 2 \\ \hat{w}_3 = \hat{w}_1^3/2 - 3\hat{w}_1/2 \end{cases}.$$

Furthermore, in cases where a notch filtering system is implemented in software or firmware of a device, an additional advantage of the apparatus described herein is that the implementation does not require redesign of other components, but rather can be accomplished using either a hardware or software update. In some example implementations, the apparatus can be implemented in software within new and existing ECG products (e.g., via a software update). Other advantages to the systems and methods described herein are apparent as well.

The above specification, examples and data provide a complete description of the manufacture and use of the composition of the invention. Since many embodiments of the invention can be made without departing from the spirit and scope of the invention, the invention resides in the claims hereinafter appended.

The invention claimed is:

1. A notch filter comprising:
a state observer unit configured to receive a sampled noisy electrical signal having a periodic noise component and a filtered electrical signal component, the state observer unit having an estimated periodic noise signal output, the estimated periodic noise signal output carrying an estimated periodic noise signal to be subtracted from the sampled noisy electrical signal, resulting in the filtered electrical signal component;
a parameter adaptation unit configured to receive the estimated periodic noise signal and an error signal from the state observer unit, the parameter adaptation unit configured to determine, based on the estimated periodic noise signal and the error signal, an updated estimated noise frequency, thereby causing the state observer unit to generate an updated estimated periodic noise signal to be provided on the estimated periodic noise signal output.

2. The notch filter of claim 1, further comprising a robustness enhancer unit having a switching output connected to the parameter adaptation unit.

3. The notch filter of claim 2, wherein the robustness enhancer unit is configured to selectively enable the parameter adaptation unit to adapt to a frequency of an estimated periodic noise signal received as part of the sampled noisy electrical signal.

4. The notch filter of claim 3, wherein the robustness enhancer unit includes a linear criterion unit and a wide angle unit.

5. The notch filter of claim 1, wherein the parameter adaptation unit receives a value defining a rate of adaptation to a frequency of the estimated periodic noise signal.

6. The notch filter of claim 1, wherein the sampled noisy electrical signal comprises an ECG signal.

7. The notch filter of claim 1, wherein the state observer unit and the parameter adaptation unit are implemented in a microcontroller of an ECG machine.

8. The notch filter of claim 1, wherein the periodic noise component of the noisy electrical signal has a frequency of about 45 Hz to about 66 Hz.

9. The notch filter of claim 1, wherein the noisy electrical signal has a sampling frequency greater than a frequency of the periodic noise component.

* * * * *